United States Patent
Arnett et al.

(10) Patent No.: US 11,279,642 B2
(45) Date of Patent: Mar. 22, 2022

(54) COMPOSITIONS AND METHODS FOR TREATING CONTAMINATED WATER

(71) Applicant: United States of America as Represented by The Secretary of the Army, Alexandria, VA (US)

(72) Inventors: Clint M Arnett, Mahomet, IL (US); Martin A Page, Urbana, IL (US); Donald M Cropek, Champaign, IL (US); Ashley N Boyd, Champaign, IL (US); Justin Lange, Mahomet, IL (US)

(73) Assignee: UNITED STATES OF AMERICA AS REPRESENTED BY THE SECRETARY OF THE ARMY, Alexandria, VA (US)

( * ) Notice: Subject to any disclaimer, the term of this patent is extended or adjusted under 35 U.S.C. 154(b) by 0 days.

(21) Appl. No.: 16/582,959

(22) Filed: Sep. 25, 2019

(65) Prior Publication Data

US 2021/0087090 A1 Mar. 25, 2021

(51) Int. Cl.
*C02F 3/34* (2006.01)
*C12N 15/75* (2006.01)

(52) U.S. Cl.
CPC ............... *C02F 3/34* (2013.01); *C12N 15/75* (2013.01)

(58) Field of Classification Search
None
See application file for complete search history.

(56) References Cited

PUBLICATIONS

Broin et al.,"Flocculent activity of a recombinant protein from Moringa oleifera Lam. seeds", Appl. Microbiol. Biotechnol. 60: 114-119 (Year: 2002).*

* cited by examiner

*Primary Examiner* — Anand U Desai
(74) *Attorney, Agent, or Firm* — Brian C. Jones

(57) ABSTRACT

A recombinant *Moringa oleifera* coagulant protein (MO) produced and secreted by *Bacillus* has coagulation/flocculation activity. The MO protein and the *Bacillus* host cells expressing the MO protein can be used in compositions and methods for treating contaminated water, such as drinking water or waste water. The MO protein can coagulate or flocculate suspended solid impurities in the water, which can then be removed.

7 Claims, 10 Drawing Sheets
Specification includes a Sequence Listing.

FIG. 9A
FIG. 9B
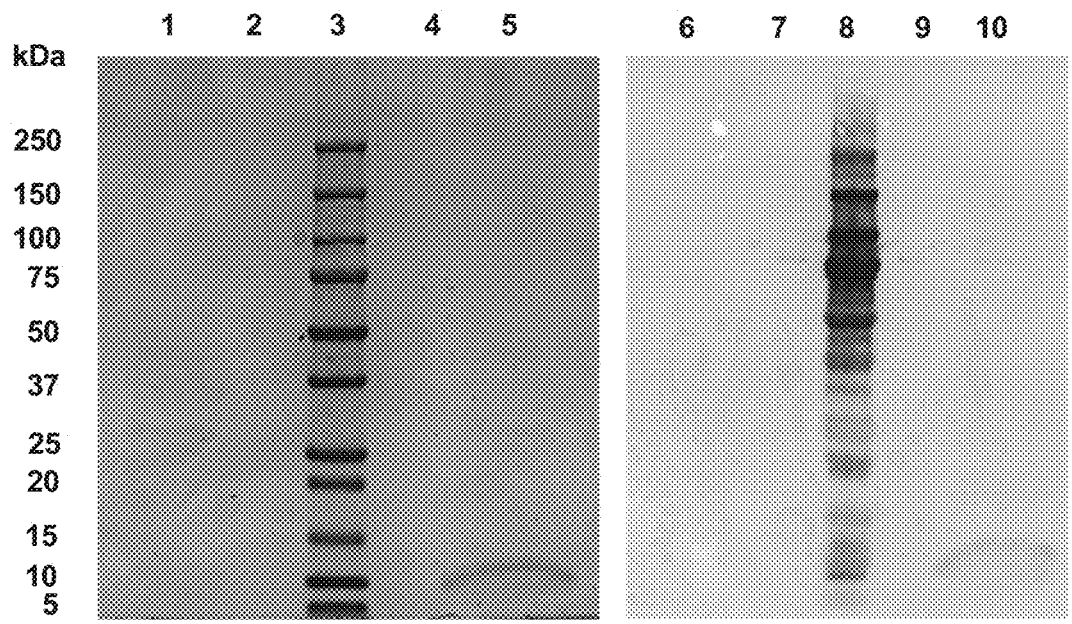
FIG. 10
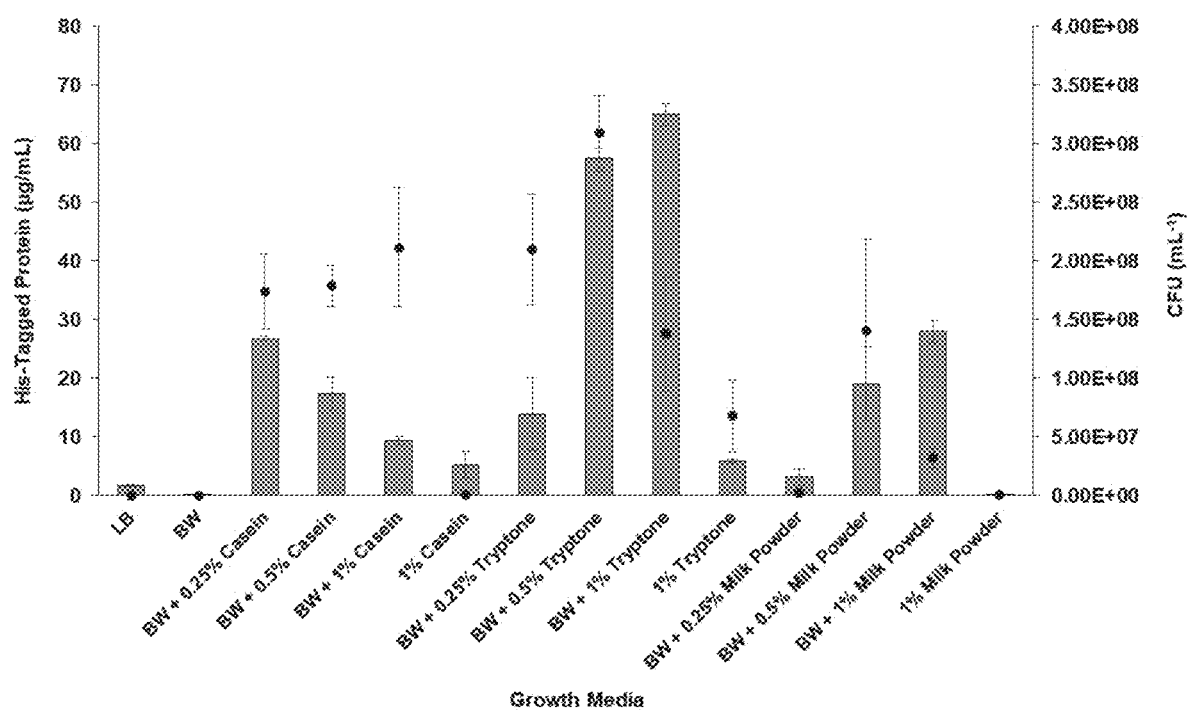

COMPOSITIONS AND METHODS FOR TREATING CONTAMINATED WATER

GOVERNMENT RIGHTS

The subject matter of this disclosure was supported in part by an appointment at the Research Participation Program administered by the Oak Ridge Institute for Science and Education through a cooperative agreement between the U.S. Department of Energy and the U.S. Army Construction Engineering Research Laboratory. Under paragraph 1(a) of Executive Order 10096, the conditions under which this invention was made entitle the Government of the United States, as represented by the Secretary of the Army, to an undivided interest therein on any patent granted by the United States. This and related patents are available for licensing to qualified licensees.

FIELD

The present disclosure relates to the expression and secretion of a recombinant *Moringa oleifera* coagulant protein (MO) in *Bacillus*, and use of the recombinant MO protein as a coagulating/flocculating agent in the treatment of contaminated water.

BACKGROUND

The costs to meet global clean water requirements on an annual basis are expected to rise to several trillion dollars in the near future depending on scarcity and overall water quality (Cazcarro et al., 2016). This is especially problematic in countries with limited resources, where an estimated two thirds of the world's population suffers from a lack of clean water (United Nations World Water Assessment Programme, 2017). In order to make water potable, it must often be treated to remove harmful agents. Additionally, wastewater should be treated before discharging it into the environment, which is a major concern due to the costs associated with removing various classes of toxic synthetic compounds (Rajasulochana and Preethy, 2016). The ever increasing global demand for clean water provides a driving force for developing new technologies to more economically treat water supplies and wastewater (Cazcarro et al., 2016).

In many water treatment processes, suspended particles are first removed using coagulation and flocculation. This is typically followed by sedimentation, filtration and chemical treatment. For coagulation and flocculation, conventional water treatment systems extensively use inorganic coagulants such as ferric and aluminum salts, and organic polymers such as polyacrylamide derivatives and polyethylene imine. Although these materials can be effective at reducing particulates and organic loads in treatment systems, they are expensive to produce, transport, and store. Their use can also lead to secondary water contamination in the form of harmful ionic iron and aluminum species, and toxic synthetic polymers (Ramavandi, 2014). Moreover, sludge produced by these coagulation processes has little secondary value due to its recalcitrant nature, which leads to additional costs associated with its disposal.

Biocoagulants such as proteins and polysaccharides are garnering attention as potential alternatives to conventional coagulants as they are regarded as nontoxic, biodegradable, and generally regarded as safe (GRAS). Also, they typically produce significantly less sludge compared to traditional coagulants, and they tend to have less influence on pH, alkalinity and conductivity, which can effect downstream treatment processes, thus lessening the need for supplemental treatment (Ndabigengesere et al., 1995; Bonin et al., 2002; Narasiah et al., 2002).

Naturally occurring coagulants capable of water clarification have been described in the literature, many of which are derived from various plant species (Yongabi, 2010; Kansal and Kumari, 2014). *Moringa oleifera* is one such species of plant that has been shown to harbor proteins within the seed that have excellent coagulation properties (Kansal and Kumari, 2014). *M. oleifera* is a drought resistant tree belonging to the family Moringaceae, which has been cultivated in developing countries for use as a nutritional supplement and food source, as well as for crude water purification for human consumption (Muyini and Evison, 1995, Ramavandi, 2014, Ravani et al., 2017). Acting as a natural coagulant, seed extracts from *M. oleifera* have been shown to dramatically improve water quality by reducing particulate content comparable to aluminum sulfate, a commonly used inorganic coagulant (Poumaye et al., 2012; De Souza Fermino et al., 2017). Purified *M. oleifera* seed proteins have been shown to clarify turbid water at doses of less than 0.5 mg/L (Ali et al., 2010).

While coagulants found in *M. oleifera* seeds can be effective, growing, harvesting and extracting the compounds from the seeds is laborious and costly, making it less practical for large-scale treatment operations (Okuda et al., 2001; Ali et al., 2010). It can take many years for *M. oleifera* to produce a high yield of seed pods, and the species proliferates only under tropical conditions making it unsuitable for growth in most of the world's climates (Ramachandran et al., 1980, Olsona, 2017).

To overcome these limitations, the expression of plant based coagulant proteins has been explored in bacteria. Broin et al. (2002) successfully cloned and expressed *M. oleifera* coagulant protein ($MO_{2.1}$) in *Escherichia coli*, which resulted in a recombinant protein capable of flocking both clays and bacteria. Suarez et al. (2002) also successfully expressed an active *M. oleifera* seed protein in *E. coli* and demonstrated the recombinant protein capable of not only flocking suspended mineral particles but also reported the protein had perceived antimicrobial activity. Furthermore, large-scale recombinant production has been demonstrated, which resulted in yields of roughly 42 mg/L of active protein and was within the concentration required for industrial use (Pavankumar et al., 2014).

Although these studies demonstrated effective production of active *M. oleifera* coagulant protein, limitations exist in the use of *E. coli* as the host for protein expression. Recombinant protein expression within *E. coli* often requires expensive inducers, and more importantly, the recombinant proteins have to be extracted from the cell cytoplasm before use. In addition, a rich growth medium is generally required to support the taxing anabolic expression process. Although effective, these methods add cost and complexity to the production process and introduce logistical burdens making them difficult to implement.

The use of *Bacillus* sp. for heterologous protein expression presents a potential alternative to expression in *E. coli*, in part due to their designation as GRAS organisms, ease of genetic modification, low nutritional requirements, large-scale growth, and production of extremely high yields of recombinant protein (Schumann, 2007). The *Bacillus* expression system can also translocate large amounts of protein into the surrounding growth media, making extraction unnecessary.

Secreted *B. subtilis* proteins are synthesized within the cytoplasm, translocated extracellularly, and released into the surrounding growth media, for example as a means to digest surrounding organic matter. This process is mediated by signal peptides (SP), which are short N-terminal amino acid sequences that act as identifiers for translocation of the attached protein out of the cell (Tjalsma et al., 2000). After the protein passes through the cell wall, the SP is removed by signal peptidases, which releases the translocated protein into the surrounding medium. The most common means for this process is via the general secretory (Sec) pathway, which includes an elaborate array of recognition factors, translocases, signal peptidases, and chaperones (Tjalsma et al., 2000; Fu et al., 2007). Thus, the Sec pathway may be used as a means to secrete a recombinant *M. oleifera* coagulant protein from *B. subtilis* when grown on both nutrient rich and nutrient limited substrates.

A need exists for a system to produce large amounts of *Moringa oleifera* coagulant protein (MO) for use in water treatment. A need also exists for improved methods for producing recombinant MO protein in *Bacillus*.

SUMMARY

The description below discloses the production and secretion of a recombinant *Moringa oleifera* coagulant protein (MO) in *Bacillus* sp., and the protein's ability to coagulate particulate material from contaminated water.

The present disclosure relates to a recombinant MO protein produced and secreted by *Bacillus* having have high coagulant activity.

The present disclosure also relates to methods for producing a recombinant MO protein that include providing a *Bacillus* cell containing a nucleic acid that encodes the MO protein fused to a *Bacillus* signal peptide (SP), and culturing the *Bacillus* cell under conditions suitable for expression of the nucleic acid and secretion of the MO protein.

The present disclosure also relates to a vector or nucleic acid construct containing a nucleic acid encoding a recombinant *Moringa oleifera* MO protein having coagulation and/or flocculation activity, a promoter sequence operably linked to the nucleic acid encoding the MO protein, and a nucleic acid encoding a *Bacillus* SP, the SP being fused or linked to the MO protein.

The present disclosure also relates to a host bacterial cell containing a vector or nucleic acid construct that encodes the recombinant MO protein fused or linked to a *Bacillus* SP.

The present disclosure also relates to a method for producing a recombinant *Bacillus* cell having enhanced secretion of MO protein by cloning a nucleic acid that encodes the MO protein fused to a *Bacillus* SP into an expression vector, and transforming a *Bacillus* cell with the vector.

The present disclosure also relates to a composition for treating contaminated drinking water, the composition containing a recombinant MO protein produced by *Bacillus*, and methods for treating contaminated drinking water using such a composition.

The present disclosure also relates to methods for treating contaminated waste water by contacting the water with the recombinant MO protein or compositions containing MO protein.

The present disclosure also relates to methods for treating contaminated waste water by adding to the water a recombinant *Bacillus* cell containing a vector or nucleic acid construct encoding a recombinant MO protein fused or linked to a *Bacillus* SP.

The present disclosure also relates to a system for enhancing production and secretion of *Moringa oleifera* MO protein in *Bacillus*, the system including a *Bacillus* cell containing a recombinant polynucleotide encoding the MO protein and a *Bacillus* SP in a suitable culture medium for expressing the nucleic acid and secreting the MO protein, wherein the nucleotide sequence is codon optimized for expression of the MO protein in bacteria at one or more codons, and wherein the MO protein is fused or linked to the SP.

BRIEF DESCRIPTION OF THE DRAWINGS

FIG. 5A is a SDS-PAGE analysis of Ni-nitrilotriacetic acid (NTA) purified cell-free extracts: lane 1, molecular weight marker; lane 2, 6×His-tagged positive control (PlyPH); lane 3, purified MO. FIG. 5B is a Western blot analysis of purified MO using 6×His-antibody probe: lane 4, PlyPH; lane 5, purified MO. FIG. 5C is a turbidity reduction analysis of seed extract, purified MO protein, and traditional coagulants aluminum sulfate and ferric sulfate, at optimal dosing concentrations. Error bars represent ±SD of 3 experimental replicates.

FIG. 7A is a graph showing protein concentration in cell-free medium over a 72 hour period. FIG. 7B (RIK1285) and FIG. 7C (pBE-S-YngK-MO) are photographs of resting cultures after 72 hour incubation viewed from the flask bottom. The inset image is the view from the top of the flask.

FIG. 8A is a graph showing the clarification (turbidity reduction) of a defined kaolin suspension using cell-free medium from pBE-S-YngK-MO over a 24 hour period. Error bars represent ±SD of 3 experimental replicates. FIG. 8B is a photograph showing the clarification of kaolin suspension after 24 hours. Left cuvette: cell-free medium from pBE-S-AprE; right cuvette: cell free medium from pBE-S-YngK-MO.

FIGS. 9A-9B show the purification of recombinant MO secreted from *B. subtilis*. FIG. 9A is SDS-PAGE analysis of NTA purified cell-free medium: lane 1, pBE-S-AprE; lane 2, blank; lane 3 MW markers; lane 4, blank; lane 5, purified MO. FIG. 9B is Western blot of purified MO using 6×His-antibody probe: lane 6, pBE-S-AprE; lane 7, blank; lane 8, MW markers; lane 9, blank; lane 10, purified MO.

FIG. 10 is a graph of cell-free 6×His-tag MO concentration and colony forming units (CFU) of pBE-S-YngK-MO grown with synthetic black water (BW) and various nutrient sources. Bars, His-tagged protein; circles, CFU; BW, black water; percentages are given as w/v and error bars represent ±SD of 3 replicates.

FIG. 11A is a graph showing reduction in turbidity in a defined kaolin suspension. Error bars represent ±SD of 3 experimental replicates. FIG. 11B is a photograph showing the clarification of kaolin suspension after 48 hrs. Left cuvette: cell-free medium from pBE-S-AprE; right cuvette: cell free medium from pBE-S-YngK-MO.

DETAILED DESCRIPTION

Figure 1:
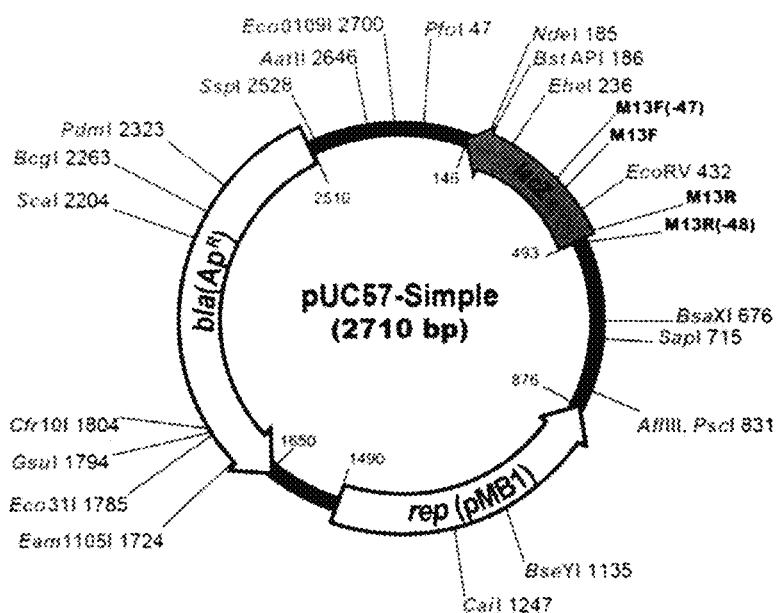
FIG. 1 is a map of the pUC57 cloning vector.

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one of the grammatical object of the article. By way of example, "an element" may mean one element or more than one element.

As used herein, "nucleic acid" refers to a nucleotide or polynucleotide sequence, and fragments or portions thereof, as well as to DNA, cDNA, and RNA of genomic or synthetic origin which may be double-stranded or single-stranded, whether representing the sense or antisense strand. It will be understood that as a result of the degeneracy of the genetic code, a multitude of nucleotide sequences may encode a given protein.

A "nucleotide sequence", "polynucleotide sequence" or a "nucleic acid sequence" as used herein refers to a succession of letters that indicate the order of nucleotides or nucleic acids within a DNA or an RNA molecule. A DNA molecule, RNA molecule or other polynucleotide sequence may be single or double stranded and may be genomic, recombinant, synthetic, a transcript, a PCR product an amplification product, an mRNA or a cDNA. These terms are also meant to encompass a sequence in either a sense or an antisense orientation and the complement thereof.

A "recombinant polynucleotide" is a polynucleotide that is not in its native state, e.g., the polynucleotide comprises a nucleotide sequence not found in nature. For example, the sequence at issue can be cloned into a vector, or otherwise combined with one or more additional nucleic acids.

As used herein, the term "*Moringa*" refers to the genus in the flowering plant family Moringaceae, also called "drumstick tree" and "horseradish tree". Species within the genus *Moringa* include *M. arborea, M. borziana, M. concanensis, M, drouhardii, M. hildebrandtii, M. longituba, M. oleifera, M. ovalfoblia, M. peregrina, M. pygmaea, M. rivae, M. ruspoliana*, and *M. stenopetala*.

As used herein, the term "*Bacillus*" or "*Bacillus* sp." refers to all species within the genus *Bacillus* as known to those of skill in the art, including but not limited to *B. alkalophilus, B. amyloliquefaciens, B. brevis, B. circulans, B. clausii, B. coagulans, B. firmus, B. lautus, B. lentus, B. licheniformis, B. megaterium, B. pumilus, B. stearothermophilus, B. subtilis*, and *B. thuringiensis*.

As used herein, the terms "MO", "MO protein" and "MO coagulant protein" refer to small storage proteins predominantly found in the seeds of *Moringa* sp., particularly *Moringa oleifera*. "$MO_{2.1}$" refers to one such MO protein, which is 60 amino acids in length identified from the seeds of *M. oleifera* and cloned by Broin et al. (2002). The terms also cover a composition containing the MO protein, which is obtainable using a method according to the present disclosure. The term also covers compositions that additionally contain the *Bacillus* bacteria according to the disclosure, or constituents thereof, and compositions that are obtainable by purifying the MO protein produced according to the disclosure.

As used herein, "percent (%) sequence identity" refers to the level of nucleic acid or amino acid sequence identity between the polynucleotide sequence that encodes any one of the disclosed polypeptides to a reference polynucleotide, or the disclosed polypeptide's amino acid sequence to a reference polypeptide, when aligned using a sequence alignment program.

BLASTN may be used to identify a polynucleotide sequence having at least 70%, 75%, 80%, 85%, 87.5%, 90%, 92.5%, 95%, 97.5%, 98%, 99%, or any percent sequence identity to a reference polynucleotide. A representative BLASTN setting optimized to find highly similar sequences uses an Expect Threshold of 10 and a Wordsize of 28, max matches in query range of 0, match/mismatch scores of 1/−2, and linear gap cost. Low complexity regions may be filtered or masked. Default settings of a Standard Nucleotide BLAST are described by and incorporated by reference to the disclosure available at blast.ncbi.nlm.nih.gov.

BLASTP can be used to identify an amino acid sequence having at least 70%, 75%, 80%, 85%, 87.5%, 90%, 92.5%, 95%, 97.5%, 98%, 99% or any percent sequence identity, or similarity to a reference amino acid. When BLASTP is used, the percent similarity is based on the BLASTP positives score and the percent sequence identity is based on the BLASTP identities score. A representative BLASTP setting uses an Expect Threshold of 10, a Word Size of 3, BLOSUM 62 as a matrix, and Gap Penalty of 11 (Existence) and 1 (Extension) and a conditional compositional score matrix adjustment. Other default settings for BLASTP are described by and incorporated by reference to the disclosure available at blast.ncbi.nlm.nih.gov The terms "wild-type", its acronym "wt", and the term "native" as used herein refer to a biological molecule that has not been genetically modified, for example, a nucleotide sequence encoding for a MO protein that exists in nature and has not been genetically modified, a MO protein translated from a coding nucleotide sequence that exists in nature and has not been genetically modified, and a vector or nucleic acid construct containing a nucleotide sequence encoding for a MO protein that exists in nature and has not been genetically modified.

As used herein, a "vector" refers to any means by which a nucleic acid can be propagated and/or transferred between organisms, cells, or cellular components. Vectors include viruses, bacteriophage, plasmids, viral vectors, expression vectors, gene transfer vectors, minicircle vectors, artificial chromosomes, and the like. Vectors can be "episomes," that is they replicate autonomously, or can integrate into a chromosome of a host cell. A vector typically contains at least an origin of replication, a cloning site and a selectable marker (e.g., antibiotic resistance). An "expression vector" refers to a vector that has the ability to incorporate and express polynucleotide sequences in a cell.

As used herein, the term "plasmid" refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell.

As used herein, the feints "promoter" or "promoter sequence" refer to a nucleic acid sequence that functions to direct transcription of a downstream gene. In embodiments, the promoter is appropriate to the host cell in which the target gene is being expressed. The promoter, together with other transcriptional and translational regulatory nucleic acid sequences (also tetined "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

As used herein, the term "operably linked" means a configuration in which a control sequence is appropriately placed (i.e., in a functional relationship) at a position relative to a polynucleotide of interest such that the control sequence directs or regulates the expression of the polynucleotide and/or polypeptide of interest.

The term "nucleic acid construct" as used herein means a nucleic acid molecule, either single-stranded or double-stranded, which is isolated from a naturally occurring gene or is modified to contain segments of nucleic acids in a manner that would not otherwise exist in nature.

As used herein, the term "transformation" refers to the process by which a vector or nucleic acid construct is introduced into a host cell. Transformation can be achieved by any one of a number of means known in the art, including chemical transformation (e.g. magnesium chloride and calcium chloride transformation) and electroporation.

The term "host cell" refers to any cell type that is susceptible to transformation, transfection, transduction, or the like with a vector or nucleic acid construct containing a polynucleotide of the present disclosure. In certain embodiments, the host cells are bacterial cells, e.g. *Bacillus* sp., and *Escherichia coli*.

As used herein, the term "amino acid" encompasses any of the twenty-two conventional proteinogenic amino acid residues (which include selenocysteine and pyrrolysine), a modified proteinogenic amino acid residue and/or a non-proteinogenic amino acid. Throughout the present disclosure, an amino acid residue may be represented by a three-letter code or a single-letter code, including but not limited to Ala (A) for alanine, Arg (R) for arginine, Asn (N) for asparagine, Asp (D) for aspartic acid, Cys (C) for cysteine, Gln (Q) for glutamine, Glu (E) for glutamic acid, Gly (G) for glycine, His (H) for histidine, Ile (I) for isoleucine, Leu (L) for leucine, Lys (K) for lysine, Met (M) for methionine, Phe (F) for phenylalanine, Pro (P) for proline, Ser (S) for serine, Thr (T) for threonine, Trp (W) for tryptophan, Tyr (Y) for tyrosine, Val (V) for valine, Pyl (O) for pyrrolysine, Sec (U) for selenocysteine.

The terms "amino acid sequence", "peptide sequence" or "protein sequence" as used herein refer to the order in which amino acid residues, connected by peptide bonds, arise in a peptide or protein chain. An amino acid sequence is generally reported from the N-terminal end containing a free amino group to the C-terminal end containing free carboxyl group.

The terms "codon-optimized" or "codon-optimization" as used herein refer to the alteration of codons in the gene or coding regions of the nucleic acid to reflect the typical codon usage of the host organism without altering the polypeptide encoded by the DNA. Such optimization includes replacing at least one, or more than one, or a significant number of, codons with one or more codons that are more frequently used in the genes of that organism.

As used herein, the term "expression" includes any step involved in the production of a polypeptide including, but not limited to, transcription, post-transcriptional modification, translation, post-translational modification, and secretion. Generally, expression includes the transcription, i.e., the synthesis of a mRNA on the basis of the DNA sequence of the gene, and the translation of the mRNA into the corresponding polypeptide chain, which may additionally be modified post-translationally.

As used herein, "water purification", "water treatment", "purifying water" or "treating water" means removing undesirable chemicals, biological contaminants, and suspended solids, from water. The goal is to produce water fit for specific purposes, such as for human consumption (drinking water), but also for a variety of other purposes, including medical, pharmacological, chemical, and industrial applications.

A first aspect of the present disclosure relates to methods for producing a recombinant *Moringa oleifera* coagulant protein (MO) in *Bacillus*. The method includes providing a *Bacillus* cell containing a recombinant nucleic acid sequence that encodes the MO protein fused to a *Bacillus* signal peptide (SP), and culturing the *Bacillus* cell under conditions suitable for expression of the nucleic acid and secretion of the MO protein.

According to various embodiments, the MO protein is $MO_{2.1}$, Genbank accession number AJ345072 (SEQ ID NO: 2), or a MO protein having 70-99% amino acid sequence identity to $MO_{2.1}$ having coagulation/flocculation activity. In an embodiment, the MO protein is encoded by a recombinant nucleic acid having the sequence of SEQ ID NO: 1, or of SEQ ID NO: 3, or a nucleic acid having 70-99% nucleotide sequence identity to SEQ ID NO: 1 or SEQ ID NO: 3, such as 70%, 75%, 80%, 85%, 90%, 92.5%, 95%, 97.5%, 98%, 99% nucleotide sequence identity.

In various embodiments, the recombinant nucleic acid encoding the MO protein has been modified for enhanced expression in bacteria by codon optimization. In some embodiments, one or more codons of the nucleic acid has been optimized for expression in *Bacillus*, for example in *Bacillus subtilis* or *Bacillus licheniformis*. Codon optimization was used to promote the highest possible level of expression in *Bacillus*. An optimization algorithm can reveal rare codons or tandem rare codons, which can reduce the efficiency of translation or even disengage the translational machinery. Codon optimization can be determined by various methods known in the art, such as with codon usage tables or using the OPTIMUMGENE™ codon optimization algorithm (GENSCRIPT®, Piscataway, N.J.), or Gene Designer (BMC Bioinformatics. 2006; 7:285).

According to various embodiments, the codon usage bias has been changed to increase the codon adaptation index (CAI). In some embodiments, the mRNA half-life was increased by optimizing the GC content, and in some embodiments, possible stem-loop structures that can adversely impact ribosomal binding and stability of mRNA have been removed.

In various embodiments, the codon-optimized nucleic acid coding for the MO protein has any possible combination of codon optimization changes to the wild-type sequence of SEQ ID NO: 1. In an embodiment, the optimized nucleic acid has the sequence of SEQ ID NO: 3, and various embodiments can have any possible combination of codon optimization changes between the sequence of SEQ ID NO: 1 and that of SEQ ID NO: 3, such as changes at about 35-40 codons. According to various embodiments, the nucleic acid has been optimized for *Bacillus* at about 1%, 5%, 10%, 15%, 20%, 25%, 30%, 40%, 50%, 60%, 70%, 80%, 90%, 95%, or 100% of the codon positions. Codons can be modified by methods known in the art (See, e.g., Welch, M., et al. (2011), Methods in Enzymology 498:43-66).

According to various embodiments, the recombinant nucleotide sequence also encodes for a *Bacillus* signal peptide (SP). In some embodiments, the SP is fused or linked to the MO protein. In some embodiments, the SP includes a SP cleavage site, which is a stretch of amino acids that is recognized and cleaved by a signal peptidase (SP cleavage site). A signal peptidase may cleave either during or after completion of translocation to generate a free signal peptide and a mature (MO) protein.

In various embodiments, the SP is one of at least 173 types of *B. subtilis* secretory signal peptides known in the art (Brockmeier et al., 2006) including, but not limited to, the group consisting of YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18).

In some embodiments, the SP is directly fused to the MO protein; in other embodiments, the SP is linked to the MO protein by a linking sequence or spacer of one or more amino acids. In some embodiments, the linking sequence contains a SP cleavage site. In various embodiments, the linking sequence or spacer is between 1 and 50 amino acids, between 2 and 25 amino acids, between 2 and 15 amino acids, between 3 and 10 amino acids, or between 3 and 5 amino acids.

A signal peptide is sometimes referred to in the art as a signal sequence, targeting signal, localization signal, localization sequence, transit peptide, leader sequence or leader peptide. Signal peptides are short N-terminal amino acid sequences that act as targets for translocation machinery and transportation across the cytoplasmic membrane. A prokaryotic SP upstream of the protein to be secreted is on average about 16-30 amino acids long and includes three regions: a positively charged N domain, a hydrophobic core region, and a hydrophilic peptidase recognition site (Tjalsma et al. 2000; Brockmeier et al. 2006). All three regions may play a role in the translocation process and may be protein specific, meaning SP action can vary significantly with different proteins. In some embodiments, at the end of the signal peptide there is a stretch of amino acids that is recognized and cleaved by a signal peptidase (SP cleavage site). A signal peptidase may cleave either during or after completion of translocation to generate a free signal peptide and a mature protein.

In some embodiments, the SP is at least one of YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18).

According to various embodiments, the *Bacillus* cell containing and expressing the recombinant nucleic acid is selected from the group consisting of *Bacillus alkalophilus*, *Bacillus amyloliquefaciens*, *Bacillus brevis*, *Bacillus circulans*, *Bacillus clausli*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, and *Bacillus thuringiensis*. In one or more embodiments, the *Bacillus* is *B. subtilis*. In other embodiments, the *Bacillus* is *B. licheniformis*.

In various embodiments, the *Bacillus* cells containing and expressing the recombinant nucleic acid is a strain optimized for the expression and secretion of heterologous proteins. In some embodiments, the cells are a low-protease *Bacillus* strain, such as, but not limited to, the *Bacillus* is *B. subtilis* strain RIK 1285, which is deficient in two kinds of proteases and therefore very suitable for secretory expression of target proteins. Other embodiments include, but are not limited to, *B. subtilis* TEB1030, *B. subtilis* CCTCC M 2016536, and *B. licheniformis* MW3.

According to various embodiments, the recombinant nucleic acid encoding the MO protein is integrated into an expression vector that further contains a promoter operably linked to the nucleic acid encoding the MO protein. The promoter sequence is not limited and several prokaryotic promoter sequences that are functional in *Bacillus* are known in the art. According to various embodiments, expression of the MO protein is controlled by a constitutive or inducible promoter. While constitutive promoters are active in all circumstances, inducible promoters are active in the cell only in response to specific stimuli, such as the presence of an external factor. Non-limiting examples of a constitutive promoter are the *B. subtilis*-derived subtilisin promoter (aprE promoter) and the β-glucanase promoter from *B. amylolyquefaciens*. Non-limiting examples of an inducible promoter are the maltose-inducible promoter from *B. subtilis* or the maltose promoter from *B. amylolyquefaciens*.

In embodiments, expression of the recombinant nucleic acid encoding the MO protein occurs via a plasmid. Plasmids are understood to be autonomously replicating DNA molecules that are extrachromosomal and do not belong to the bacterial chromosome. In some embodiments, the plasmid is present in a host cell in more than one copy, such as more than five copies, more than ten copies or more than 20 copies. According to another embodiment, the nucleic acid is integrated into a chromosome of the *Bacillus* cell. In another embodiment, the nucleic acid is contained on an extrachromosomal element.

According to various embodiments, the recombinant MO protein additionally includes an affinity tag, which allows interaction with a specific material and thus binds the MO protein to this material, and contaminants or by-products can be removed by washing. In one embodiment, the nucleic acid sequence that encodes the affinity tag is attached to the 3' end of the sequence that encodes the MO protein, so that the affinity tag is fused to the C terminal of the MO protein. In another embodiment, the nucleic acid sequence that encodes the affinity tag is attached to the 5' end of the sequence that encodes the MO protein, so that the affinity tag is fused to the N terminal of the MO protein.

In some embodiments, an amino acid spacer is included between the affinity tag and the recombinant MO protein. In various embodiments, the spacer is not more than 20, not more than 10, or not more than 5 amino acids in length. In some embodiments, the spacer contains the recognition sequence of a specific protease to be able to split off the affinity tag and the spacer or parts of the spacer from the MO protein. In an embodiment, the affinity tag is a polyhistidine-Tag, such as a 6×His-Tag.

According to various embodiments of the method for producing the MO protein, the *Bacillus* host cells are cultivated using a fed-batch protocol. In this case, fed-batch is understood to mean that a portion of the nutrients is already present at the beginning of the cultivation and a further portion of the nutrients is added continuously or discontinuously from a specific point in time. In other embodiments, the *Bacillus* host cells are cultivated using a batch protocol. In this case, batch is understood to mean that all the nutrients are already present at the beginning of cultivation and no further nutrients are added during cultivation.

For industrial-scale production of the recombinant MO protein, in various embodiments, the *Bacillus* host cells are cultured in fermenters that are adapted accordingly to the metabolic properties of the cells. During the culture, the host cells metabolize the supplied substrate and form the desired product (i.e., MO protein), which, after the end of fermentation, in some embodiments, is separated from the production organisms and is purified and/or concentrated from the fermenter slurry and/or the fermentation medium. In some embodiments, methods for producing the recombinant MO protein do not include a purification step that serves for the targeted separation of the MO protein. Also, some embodiments include recombinant MO preparations obtainable by the present method that does not include a purification step that serves for the targeted separation of MO protein.

According to various embodiments, the presently disclosed methods lead to a high yield of MO protein. At least 50 mg, at least 100 mg, at least 200 mg, at least 500 mg, or more than 500 mg of MO protein per liter of culture medium are achieved.

A second aspect of the present disclosure relates to a recombinant *Moringa oleifera* MO protein that is produced and secreted by *Bacillus*. According to embodiments, the recombinant MO protein is produced by methods provided in the present disclosure. In an embodiment, the MO protein is $MO_{2.1}$, Genbank accession number A1345072 (SEQ ID NO: 2), or a MO protein having 90-99% amino acid sequence identity to $MO_{2.1}$, having coagulation/flocculation activity.

According to various embodiments, the recombinant MO protein further includes a *Bacillus* SP. The SP is at least one of at least 173 types of *B. subtilis* secretory signal peptides known in the art (Brockmeier et al., 2006), including, but not limited to, the group consisting of YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18). In some embodiments, the SP is fused or linked to the MO protein. In some embodiments, the SP includes a SP cleavage site, which is a stretch of amino acids that is recognized and cleaved by a signal peptidase (SP cleavage site).

According to various embodiments, the recombinant MO protein further includes an affinity tag. In one embodiment, the affinity tag is attached to the C terminal of the MO protein. In another embodiment, the affinity tag is attached to the N terminal of the MO protein. In some embodiments, an amino acid spacer is included between the affinity tag and the MO protein. In various embodiments, the spacer is not more than 20, not more than 10, or not more than 5 amino acids in length. In some embodiments, the spacer contains the recognition sequence of a specific protease to be able to split off the affinity tag and the spacer itself or parts of the spacer from the MO protein. In an embodiment, the affinity tag is a polyhistidine-Tag, such as a 6×His-Tag.

A third aspect of the present disclosure relates to a vector or nucleic acid construct that includes a nucleic acid encoding a recombinant MO protein. According to various embodiments, the vector or nucleic acid construct includes a promoter sequence that is operably linked to the nucleic acid encoding the recombinant MO protein.

In some embodiments, the vector or nucleic acid construct also includes a nucleic acid encoding a *Bacillus* SP, the SP being fused or linked to the MO protein. According to various embodiments, the nucleic acid encoding the SP is selected from the group consisting of: YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18).

According to various embodiments, the nucleic acid encoding the recombinant MO protein has been codon optimized for enhanced expression of the recombinant MO protein in bacteria at one or more codons. In some embodiments, the nucleic acid has been optimized for enhanced expression in *Escherichia*, for example *E. coli*. In some embodiments, the nucleic acid has been optimized for enhanced expression in *Bacillus*, for example *B. subtilis* or *B. licheniformis*. SEQ ID NO: 1 is a wild-type sequence encoding the $MO_{2.1}$ protein. In various embodiments, the nucleic acid coding for the recombinant MO protein is the wild-type sequence of SEQ ID NO: 1 that has been further codon optimized for enhanced expression in bacteria at any possible combination of codon optimization changes, such as 1, 2, 5, 10, 15, 20, 25, 30, 35, 40, 45, 50, 55, 60, or all the codons. According to various embodiments, the nucleic acid coding for the recombinant MO protein has been optimized for *Escherichia* or *Bacillus* at about 1%, 5%, 10%, 15%, 20%, 25%, 30%, 40%, 50%, 60%, 70%, 80%, 90%, 95%, or 100% of the codon positions.

In SEQ ID NO: 3, the nucleic acid encoding the recombinant MO protein has been codon optimized for expression in bacteria, in particular *E. coli*, at multiple codons. In one embodiment, the optimized nucleic acid has the sequence of SEQ ID NO: 3, and various embodiments have any possible combination of codon optimization changes between the wild-type sequence of SEQ ID NO: 1 and that of SEQ ID NO: 3, such as about 35-40 codons. In embodiments, the nucleic acid encoding the recombinant MO protein has at least 70% sequence identity to SEQ ID NO: 1 or SEQ ID NO: 3, such as 70%, 75%, 80%, 85%, 90%, 92.5%, 95%, 97.5%, 98%, or 99% sequence identity.

According to various embodiments, the vector or nucleic acid construct also includes a selectable marker gene. In embodiments, the promoter that is operably linked to the nucleic acid encoding the MO protein is a constitutive promoter, such as the aprE promoter; in other embodiments, the promoter is an inducible promoter.

In various embodiments, the vector or nucleic acid construct is the pBE-S DNA vector containing a nucleic acid encoding the recombinant MO protein and SP as presently disclosed. In embodiments, the vector or nucleic acid construct also encodes for an affinity tag fused or linked to the MO protein.

A fourth aspect of the present disclosure relates to a host bacterial cell containing a vector or nucleic acid construct that includes a nucleic acid encoding a recombinant *Moringa oleifera* MO protein. In some embodiments, the vector or nucleic acid construct also includes a nucleic acid encoding a *Bacillus* SP, the SP being fused or linked to the MO protein.

According to various embodiments, the nucleic acid encoding the recombinant MO protein has been codon optimized for enhanced expression of the recombinant MO protein in bacteria, at one or more codons. In some embodiments, the nucleic acid has been optimized for enhanced expression in *Escherichia*, for example *E. coli*. In some embodiments, the nucleic acid has been optimized for *Bacillus*, for example *B. subtilis* or *B. licheniformis*. SEQ ID NO: 1 is a wild-type sequence encoding the $MO_{2.1}$ protein. In various embodiments, the nucleic acid coding for the recombinant MO protein is the wild-type sequence of SEQ ID NO: 1 that has been codon optimized for enhanced expression in bacteria at any possible combination of codon optimization changes, such as 1, 2, 5, 10, 15, 20, 25, 30, 35, 40, 45, 50, 55, 60, or all the codons. According to various embodiments, the nucleic acid coding for the recombinant MO protein has been optimized for *Escherichia* or *Bacillus* at about 1%, 5%, 10%, 15%, 20%, 25%, 30%, 40%, 50%, 60%, 70%, 80%, 90%, 95%, or 100% of the codon positions.

In SEQ ID NO: 3, the nucleic acid of SEQ ID NO: 1 has been codon optimized for expression of the MO protein in bacteria at multiple codons. In various embodiments, the optimized nucleic sequence has any possible combination of codon optimization changes between the wild-type sequence of SEQ ID NO: 1 and that of SEQ ID NO: 3, such as about 35-40 codons. In embodiments, the nucleic acid encoding the recombinant MO protein has at least 70% sequence identity to SEQ ID NO: 1 or SEQ ID NO: 3, such as 75%, 80%, 85%, 90%, 92.5%, 95%, 97.5%, 98%, or 99% sequence identity.

According to embodiments, the recombinant bacterial cell contains one or more copies of the vector or nucleic acid construct encoding the recombinant MO protein. In embodiments, the vector or nucleic acid construct is contained in a chromosome of the bacterial cell. In some embodiments, the vector or nucleic acid construct is contained as an extrachromosomal element.

According to various embodiments, the host bacterial cell is a *Bacillus* cell. In embodiments, the host bacterial cell is a *B. alkalophilus, B. amyloliquefaciens, B. brevis, B. circulans, B. clausli, B. coagulans, B. firmus, B. lautus, B. lentus, B. licheniformis, B. megaterium, B. pumilus, B. stearothermophilus, B. subtilis,* or *B. thuringiensis* cell. In an embodiment, the host bacterial cell is a *B. subtilis* cell. In another embodiment, the host bacterial cell is an *Escherichia coli* cell.

A fifth aspect of the present disclosure relates to a method of producing a recombinant *Bacillus* cell having enhanced secretion of recombinant *Moringa oleifera* MO protein. According to various embodiments, the method includes cloning a recombinant nucleic acid encoding the MO protein fused to a *Bacillus* SP into an expression vector, and transforming a *Bacillus* cell with the expression vector containing the cloned recombinant nucleic acid.

In various embodiments, the nucleic acid encoding the recombinant MO protein is codon optimized for expression of the MO protein in bacteria. In various embodiments, the optimized nucleic sequence has any possible combination of codon optimization changes between the wild-type sequence and that of the codon optimized sequence, such as changes at any 1, 2, 5, 10, 15, 20, 25, 30, 35, 40, 45, 50, 55, 60 or more codons, or at 1%, 5%, 10%, 15%, 20%, 25%, 30%, 40%, 50%, 60%, 70%, 80%, 90%, 95% or 100% of the codon positions.

According to various embodiments, the MO protein is $MO_{2.1}$. In embodiments, the nucleic acid encoding the recombinant MO protein is the wild-type sequence of SEQ ID NO: 1. In other embodiments, the nucleic acid encoding the MO protein is a sequence having one or more codons of SEQ ID NO: 1 optimized for expression of the recombinant MO protein in bacteria. In some embodiments, the nucleic acid encoding the recombinant MO protein is the codon optimized sequence of SEQ ID NO: 3. Other embodiments have an optimized nucleic acid sequence with any possible combination of codon optimization changes between the wild-type sequence of SEQ ID NO: 1 and that of SEQ ID NO: 3, such as about 35-40 codons. In embodiments, the nucleic acid encoding the recombinant MO protein has at least 70% sequence identity to SEQ ID NO: 1 or SEQ ID NO: 3, such as 70%, 75%, 80%, 85%, 90%, 92.5%, 95%, 97.5%, 98%, or 99% sequence identity.

According to various embodiments, the SP is one of at least 173 types of *B. subtilis* secretory signal peptides known in the art. In various embodiments, the SP is at least one selected from the group consisting of YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17) and YusW (SEQ ID NO: 18).

According to various embodiments, the *Bacillus* is *B. alkalophilus, B. amyloliquefaciens, B. brevis, B. circulans, B. clausli, B. coagulans, B. firmus, B. lautus, B. lentils, B. licheniformis, B. megaterium, B. pumilus, B. stearothermophilus, B. subtilis,* or *B. thuringiensis*. In an embodiment, the *Bacillus* is *B. subtilis*. In another embodiment, the *Bacillus* is *B. licheniformis*.

According to various embodiments, the recombinant nucleic acid also encodes for an affinity tag linked or fused to the MO protein. In some embodiments, the affinity tag is a His-tag, such as a 6×His-tag.

Embodiments of the method of producing a recombinant *Bacillus* cell having enhanced secretion of MO protein include screening potential *Bacillus* cells by an assay, such as an immunological assay, such as an ELISA, to rapidly screen hundreds of clones for secretion of the MO protein. In some embodiments, the ELISA utilizes a primary antibody to a tag component of the recombinant MO protein, such as anti-6×His-tag antibody.

A sixth aspect of the present disclosure relates to a composition for treating contaminated drinking water, the composition containing a recombinant *Moringa oleifera* MO protein produced and secreted by bacteria. According to various embodiments, the MO protein is produced and secreted by *Bacillus*, such as any of *B. alkalophilus, B. amyloliquefaciens, B. brevis, B. circulans, B. clausli, B. coagulans, B. firmus, B. lautus, B. lentus, B. licheniformis, B. megaterium, B. pumilus, B. stearothermophilus, B. subtilis,* or *B. thuringiensis*. In an embodiment, the recombinant MO protein is produced and secreted by *B. subtilis*.

In various embodiments, in addition to the recombinant MO protein, the composition contains one or more additional ingredients for treating the contaminated water, such as one or more coagulant, flocculent, disinfectant or coagulant aid.

In some embodiments, the composition is in a unit dosage form for treating a relatively small amount of contaminated drinking water. By relatively small amount is meant a volume of water typically required for immediate consumption in domestic or personal use, or which is required for short term storage and consumption. In embodiments, the relatively small amount of contaminated drinking water is a volume of about 0.1 to 100 liters of water, or about 0.5 to 40 liters, about 5 to 20 liters, about 1 to 5 liters, or about 2 to 10 liters.

In some embodiments, the unit dosage of the composition is in a form of a solid powder, granules, or a tablet. In some embodiments, the unit dosage is contained in a water soluble single or multi-compartment pouch or a single or multi-compartment sachet that is opened prior to use.

According to various embodiments of the composition, the recombinant MO protein has an affinity tag, such as a His-Tag. In some embodiments, the recombinant MO protein has undergone one more purification steps that utilize the affinity tag. In some embodiments, the recombinant MO protein includes a *Bacillus* SP fused or linked to the MO protein.

A seventh aspect of the present disclosure relates to a method for treating contaminated drinking water that includes contacting the water with an effective amount of a composition containing a recombinant *Moringa oleifera* MO protein produced and secreted by bacteria. According to various embodiments, the recombinant MO protein is produced and secreted by *Bacillus*, such as any of *B. alkalophilus, B. amyloliquefaciens, B. brevis, B. circulans, B. clausli, B. coagulans, B. firmus, B. lautus, B. lentos, B. licheniformis, B. megaterium, B. pumilus, B. stearothermophilus, B. subtilis*, or *B. thuringiensis*. In an embodiment, the recombinant MO protein is produced and secreted by *B. subtilis*.

According to various embodiments, the method includes contacting the composition to the contaminated drinking water to obtain partially purified water containing coagulated and/or flocculated solid matter, and then removing at least part of the solid matter by one or more of sedimentation, filtration, decanting, flotation, or a combination thereof, to obtain purified water.

According to various embodiments, some methods for treating the contaminated drinking water are for the batch-wise purification and clarification of a relatively small predetermined volume of contaminated drinking water. The method includes adding an effective amount of the present composition in unit dosage form to the predetermined volume of contaminated water, stirring the water to disperse the composition and to flocculate and coagulate suspended solid impurities therein, allowing the stirred water to stand, and thereafter filtering the water to remove the impurities and to obtain purified water suitable for human consumption. In embodiments, the relatively small predetermined volume of water is in a range of about 0.1 to 100 liters, or about 0.5 to 40 liters, about 5 to 20 liters, about 1 to 5 liters, about 2 to 10 liters, or about 0.5 to 2 liters.

Another aspect of the present disclosure relates to a method for treating contaminated water that includes contacting the water with an effective amount of recombinant *Bacillus* cells, the cells containing a vector or nucleic acid construct encoding a recombinant *Moringa oleifera* MO protein fused or linked to a *Bacillus* signal peptide (SP), the recombinant *Bacillus* cells expressing and secreting the recombinant MO protein. The MO protein has coagulation and/or flocculation activity. In various embodiments, the recombinant *Bacillus* cells are any of *B. alkalophilus, B. amyloliquefaciens, B. brevis, B. circulans, B. clausli, B. coagulans, B. firmus, B. lautus, B. lentils, B. licheniformis, B. megaterium, B. pumilus, B. stearothermophilus, B. subtilis*, or *B. thuringiensis*. In one embodiment, the *Bacillus* cells include *B. subtilis*.

According to various embodiments, the vector or nucleic acid construct encoding the recombinant MO protein comprises SEQ ID NO: 1, or a sequence having one or more codons of SEQ ID NO: 1 optimized for enhanced expression of the recombinant MO protein in *Bacillus*. In some embodiments, the vector or nucleic acid construct encoding the MO protein contains the sequence of SEQ ID NO: 3, or a sequence having at least 70% sequence identity to SEQ ID NO: 3. In some embodiments, the SP is at least one selected from the group consisting of: YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18).

According to various embodiments, the recombinant *Bacillus* cells expressing and secreting the recombinant MO protein are capable of growing and/or dividing, and/or expressing and secreting the MO protein, in the contaminated water. In various embodiments, the contaminated water is wastewater, which is any water that has been affected by human or animal use. In various embodiments, wastewater is used water from any combination of domestic, industrial, commercial or agricultural activities, surface runoff or storm water, and any sewer inflow or sewer infiltration. Types of wastewater include: domestic wastewater from households, municipal wastewater from communities (also called sewage) and industrial wastewater from industrial activities.

Examples

Materials and Methods

Routine methods such as DNA isolation, restriction and ligation were performed using standard protocols (Sambrook J, et al. 2001).

Cloning and Expression of MO Protein in *E. coli.*

Figure 2:
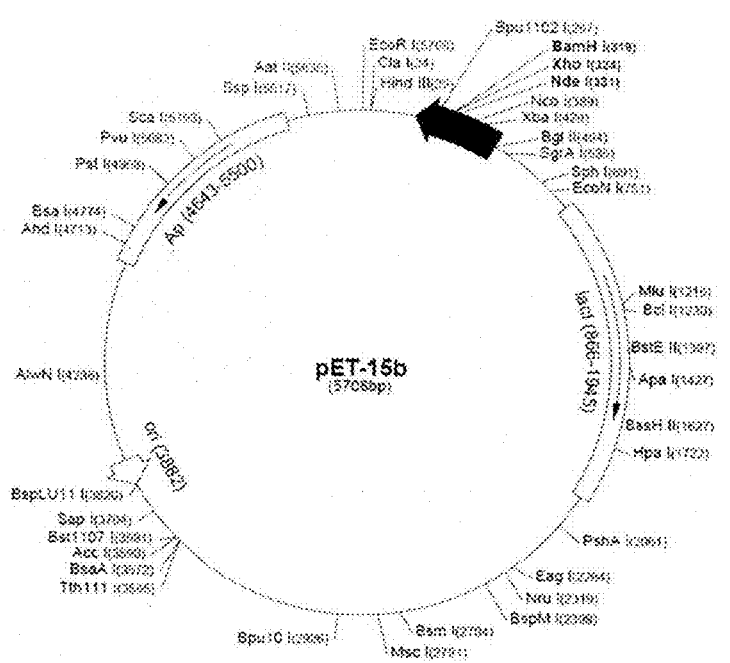
FIG. 2 is a map of the pET-15b *E. coli* expression vector.
Figure 2:
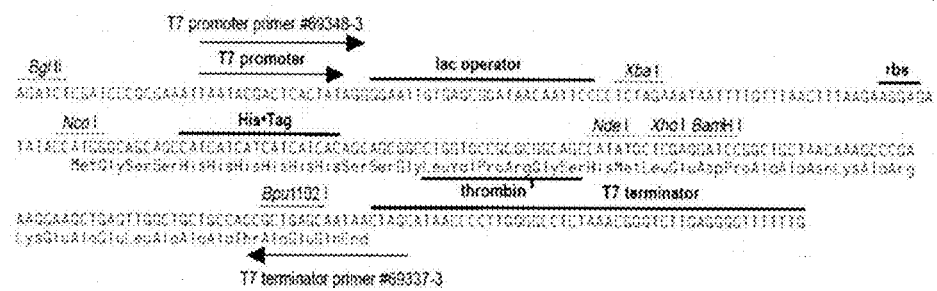

The *M. oleifera* coagulant protein (MO) gene sequence was obtained from the National Center for Biotechnology Information (NCBI) database (Accession No. AJ345072) (SEQ ID NO: 1). The gene sequence was codon enhanced for expression in bacteria using the OPTIMUMGENE™ codon optimization algorithm (GENESCRIPT®, Piscataway, N.J.) (SEQ ID NO: 3). The optimized MO gene was synthesized using de novo oligonucleotide chemistry, cloned into pUC57 (SEQ ID NO: 29) (FIG. 1) for archival purposes, and then subcloned into a pET-15b expression vector (SEQ ID NO: 30) (FIG. 2) using the BamHI restriction sites. Both vectors containing the codon optimized MO gene were propagated in chemically competent *E. coli* and purified using a commercially available plasmid mini-preparation kit. The MO coagulant protein gene sequences in both vectors were confirmed by DNA sequencing using standard BIGDYE® chemistry (ThermoFisher Scientific).

To test the expression and coagulation activity of MO, the protein was initially expressed using the well characterized lac operon of *E. coli*. Chemically competent ONE SHOT® BL21(DE3) cells (Invitrogen, Carlsbad, Calif.) were transformed and induced according to the manufacturer's protocol, with the exception that a 0.1% inoculum was used to start cultures for coagulant gene expression. Cultures were grown to an optical density at 600 nm ($OD_{600}$) of roughly 0.3 and then induced by the addition of isopropyl β-D-1-thiogalactopyranoside (IPTG) to a final concentration of 0.5 mM for 2 hrs. The bacterial cultures were harvested by centrifugation and proteins were extracted with a combination of lysis buffer (100 mM Tris pH 8, 500 mM NaCl, 10% glycerol, 25 mM imidazole, 1 mM PMSF, and 40 mM DTT) and sonication. The total lysate was then centrifuged and the supernatant was dialyzed against 50 mM $Na_2HPO_4$, pH 7.0 and 150 mM NaCl overnight at 4° C. The sample was then applied to a Ni-nitrilotriacetic acid (NTA) agarose column (Qiagen, Valencia, Calif.) and the 6×His-tagged fusion protein was affinity purified by eluting with 250 mM imidazole and dialyzed as previously described.

Purified recombinant protein was quantified using a QUBIT™ Protein Assay (Invitrogen) and subsequently analyzed by sodium dodecyl sulfate-polyacrylamide gel electrophoreses (SDS-PAGE) using a 4-20% polyacrylamide gel. A Western blot was performed to confirm the presence of 6×His-tagged protein by transferring proteins onto a 0.2 µm polyvinylidene difluoride (PVDF) membrane using a TRANS-BLOT® TURBO™ Transfer System per the manufactures recommendations (Bio-Rad, Hercules, Calif.). Fusion proteins were probed using a Bio-Rad IMMUN-BLOT® Assay Kit (Bio-Rad cat. #1706461) with a 1:1000 dilution of anti-6×His-tag IgG primary antibody (Bio Rad cat. #6200203) per the manufacturer's protocol. *Bacillus* lytic enzyme PlyPH tagged with N and C-terminus 6×His-tags served as a positive control for the protein immunoblot.

*M. oleifera* Seed Extract and Inorganic Coagulants.

*M. oleifera* seeds were obtained from Moringa Farms (Sherman Oaks, Calif.) and extracted by crushing whole seeds with a pestle and mortar and mixing 1:100 (w/v) in deionized water. The suspension was shaken vigorously for 5 minutes and then allowed to settle. After 5 minutes, the supernatant was filtered through a tissue to remove remaining debris. Inorganic coagulants tested were prepared to a 10 mg/mL stock solution in water, with the exception of ferric chloride which was prepared to a 10 mg/mL in 0.1 mM HCl. The resulting crude seed extract and inorganic stock solutions were tested for their ability to clarify turbid water as described below.

Coagulation Activity.

Coagulation activities of the recombinant MO protein, seed extract biocoagulants and the traditional inorganic coagulants were determined using a buffered kaolin suspension containing 10 g/L kaolin in 1 mM $NaHCO_3$. The suspension was mixed in a test buffer solution containing 1 mM $NaHCO_3$ and 1 mM NaCl to a final kaolin concentration of 0.1%, which resulted in turbidity of roughly 250 nephelometric turbidity units (NTU) and an optical density at 500 nm ($OD_{500}$) of approximately 0.35. Various concentrations of coagulants were added to 10 mL glass vials containing the buffered kaolin suspension and stirred at 200 rpm for 1 min and at 15 rpm for 20 min. Stirring was then stopped and the suspension was allowed to settle for 1 hr before measuring the turbidity using a LaMotte LTC3000 turbidity meter (Chestertown, Md.).

A small scale coagulation assay was also developed based on the method used by Ghebremichael et al. (2005). Specifically, coagulation of the buffered kaolin suspension described above was carried out in 4 mL polyethylene cuvettes, where various concentrations of coagulants were added to a total volume of approximately 2.5 mL. Reactions were mixed end-over-end at 100 rpm in a rotating mixer for 1 min, and then speed was decreased to 10 rpm for 20 min after which the samples were allowed to settle for predetermined time points at 24° C. After settling, $OD_{500}$ was read using a UV-Vis spectrophotometer. Activity for both assays was measured as a function of coagulant concentration and reduction in NTU or $OD_{500}$.

Cloning and Expression of MO Protein in *Bacillus*.

Figure 3:
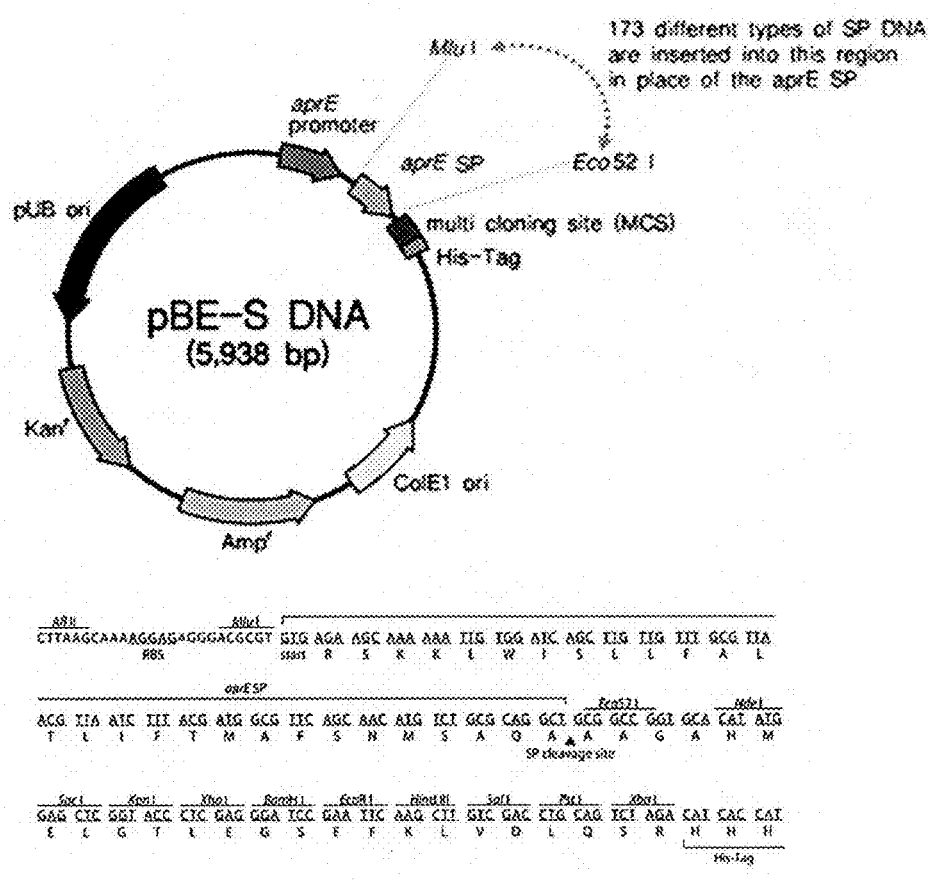
FIG. 3 is a map of the pBE-S DNA expression vector, which includes the pUB 110-derived replication ori (pUB ori) and a kanamycin-resistance gene (Kan$^r$) that function in *B. subtilis*, as well as the pUC-derived replication ori (ColE1 ori) and an ampicillin-resistance gene (Amp$^r$) that function in *E. coli*. Additionally, pBE-S DNA includes a *B. subtilis*-derived subtilisin promoter (aprE promoter) and secretory signal peptide (aprE SP), which are located upstream from a multi-cloning site (MCS) for the secretion target protein (MO protein) and a 6×His-Tag sequence. Different types of signal peptides (SP) can be cloned in pBE-S DNA constructs via the MluI and Eco521 sites, replacing the aprE SP.

After confirmation of active MO in *E. coli*, the same optimized gene (SEQ ID NO: 3) was cloned and expressed in *B. subtilis*. The gene was polymerase chain reaction (PCR) amplified from the pUC57 construct using primers (SEQ ID NO: 25, SEQ ID NO: 26) designed with the IN-FUSION® Cloning Primer Design Tool (Takara Bio, Mountain View, Calif.) to meet the downstream requirements for integration into pBE-S DNA vector (SEQ ID NO: 31) at NdeI and XbaI restriction sites (FIG. 3). The resulting PCR product was purified by gel electrophoresis and cloned into the multiple cloning site (MCS) of pBE-S, transformed into chemically competent *E. coli*, and purified using a commercially available plasmid mini-preparation kit. The resulting construct was named pBE-S-MO. Correct gene sequence and orientation within the plasmid were confirmed via DNA sequencing using MO gene sequencing forward and reverse primers (SEQ ID NO: 27, SEQ ID NO: 28).

Figure 4:
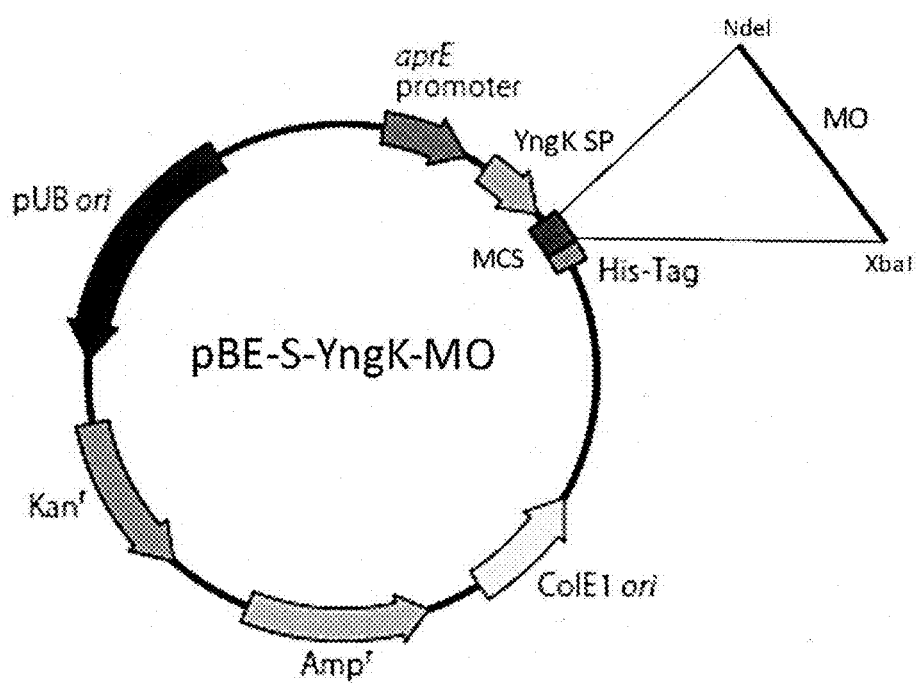
FIG. 4 is a map of pBE-S-YngK-MO, which is an embodiment that includes the YngK SP and MO protein, cloned in pBE-S DNA.

To create the random SP clone library, pBE-S-MO was digested with MluI and EagI (isoschizomer of Eco521) and gel purified. The linearized DNA was used to randomly ligate and transform 173 different *B. subtilis* SP (Takara Bio) into chemically competent *E. coli*. Roughly 2000 antibiotic resistant transformants were pooled and pBE-S-MO harboring random SP were extracted, purified, and transformed into chemically competent *B. subtilis* strain RIK1285. Cells were plated on selective medium, and 440 random clones were propagated and screened for the presence of heterologous protein within the cell-free medium using a 96-well Cell Biolabs His-Tag Protein ELISA Kit (San Diego, Calif.) per the manufacturer's instructions. Absorbance at 450 nm was read using a microplate reader, and concentrations of tagged protein were quantitated using a standard curve generated with known concentrations of 6×His-tagged Rhotekin (MW 10 kDa). Concentrations were standardized against cell-free medium from the wild type RIK1285. Signal peptides of clones that secreted 6×His-tagged protein into the medium were identified by plasmid extraction, DNA sequencing, and alignment to known *Bacillus* SP sequences. Nomenclature for MO secreting clones was given as pBE-S-SP-MO. An example is shown in FIG. 4, pBE-S-YngK-MO.

Characterization of SP.

After SP identification by DNA sequencing, physical traits of each SP were determined and analysis of variance (ANOVA) and linear regression analysis were performed to identify any statistically relevant correlations between the SP characteristics identified and amount of secreted MO protein. SignalP 4.1, with a cutoff of 0.450, was used to calculate D-scores (Petersen et al., 2011). Net charges were determined by Protein Calculator v3.4 (Chris Putnam, The Scripps Research Institute, U.S.A.) at neutral pH. Isoelectric point (pI) and grand average of hydropathicity (GRAVY) were calculated using ProtParam (Gasteiger et al., 2005). Peptide hydrophobicity was determined by dividing the total number of hydrophobic amino acids by the total number of residues.

Sequences of truncated SP were determined by removing N-terminus amino acids directly downstream from the translational start site until the D-scores were <0.450. The resulting truncated SP gene sequences were then synthesized using de novo oligonucleotide chemistries and cloned into pBE-S-MO as described previously.

Analysis of MO Protein Coagulation Activity.

Cell-free medium from 100 mL cultures of pBE-S-YngK-MO and pBE-S-AprE (no MO gene) grown with LB were studied for their ability to clarify turbid water. After 48 hrs at 37° C. with shaking (180 rpm), the cells were removed from the culture by centrifugation and the resulting cell-free medium was concentrated by spin filtration to 25× and 40× of the eluent volume. Protein concentrations were determined using the method of Bradford (Bradford, 1976) and activity was evaluated using the small-scale coagulation assay described above. To confirm the presence of recombinant MO, concentrated cell-free media was purified by affinity chromatography and immunoblotted as previously described.

In addition to LB, growth and coagulation activity of cell-free medium was also evaluated with a mixture of synthetic black water amended with various concentrations of casein, tryptone, and milk powder (0.25-1% w/v). The defined synthetic black water was adapted from Nopens et al. (2001), and contained the following in diH$_2$O: beef extract, 360 mg/L; milk powder, 360 mg/L; urea, 180 mg/L; NH$_4$Cl, 150 mg/L; yeast extract, 480 mg/L; humic acid, 60 mg/L; K$_2$HPO$_4$, 422 mg/L; NaCl, 350 mg/L; standard test dust, 10 mg/L; and common top soil, 6 mg/L. This formulation resulted in a solution having a target chemical oxygen demand (COD) of roughly 1200 mg/L. The synthetic black water was steam sterilized at 120° C. for 20 min prior to use. Five mL cultures were grown for 48 hrs as previously described in the defined media, cells were removed by centrifugation, and 6×His-tagged recombinant proteins were detected in the cell-free media using ELISA as described previously. Colony forming units (CFU) were used to estimate biomass by reconstituting pellets in sterile water, serially diluting, and plating onto LB.

Results

Evaluation of Prokaryotic Gene Optimization of MO

Figures 5A, 5B:
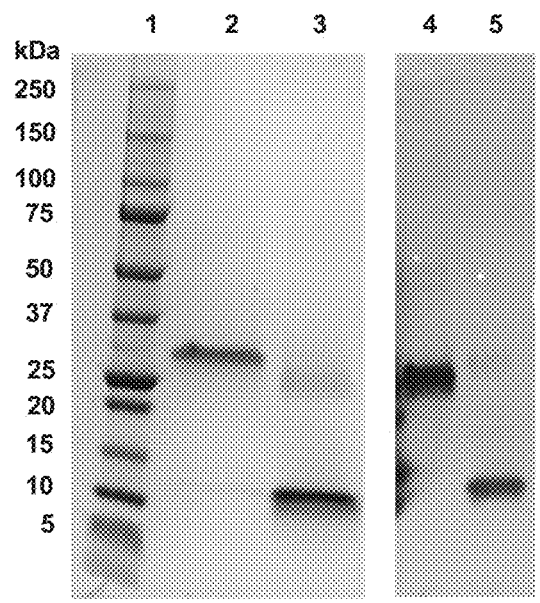
FIGS. 5A-5C show the purification and coagulant activity of recombinant MO protein expressed in *E. coli*.

To evaluate activity of the codon optimized MO gene sequence (SEQ ID NO: 3), it was initially expressed in *E. coli* due to the relative ease of transformation and predictable ITPG induction. As shown by SDS PAGE in FIG. 5A, expression and subsequent NTA purification of the *E. coli* cell lysate resulted in a band having approximately the same molecular weight as the 6×His-tagged MO, 9.6 kDa (lane 3) Western blot analysis shown in FIG. 5B confirmed the presence of the His epitope tag (lane 5). The protein was roughly 84% pure based on SDS-PAGE analysis and a total yield of roughly 0.6 mg/L was achieved.

Figure 5C:
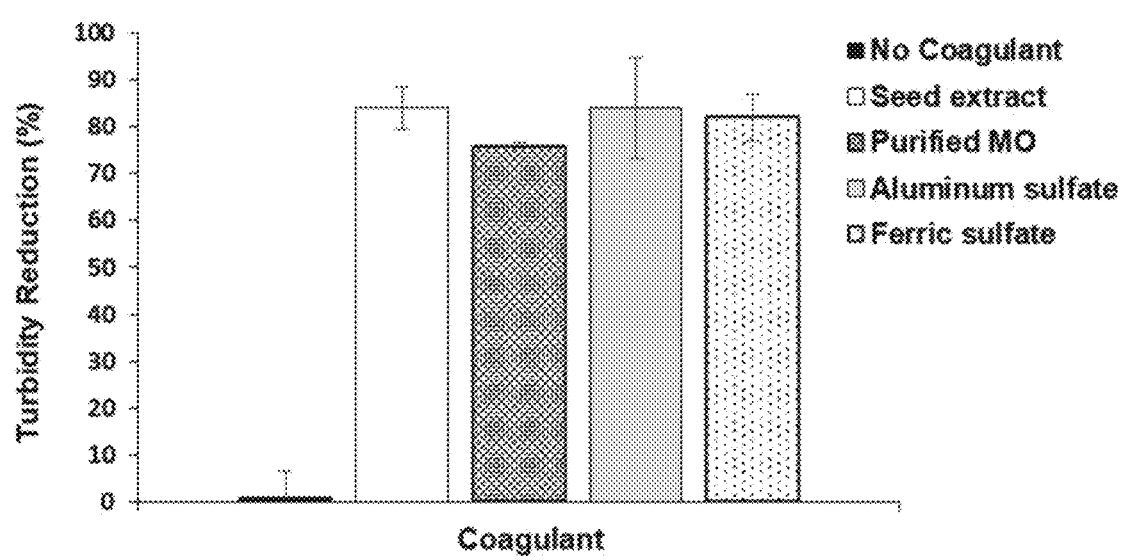

Coagulant activity of the *E. coli* expressed MO was evaluated as the ability to reduce NTU in a kaolin suspension. No effect on clarification was observed with the purified MO until a dosing concentration >20 mg/L was achieved (data not shown). At 30 mg/L, approximately an 80% reduction in turbidity was observed compared to unamended controls, and additional dosing up to 60 mg/L showed no significant increase in clarification. As shown by graph results in FIG. 5C, when compared to traditional inorganic coagulants, the recombinant MO protein was capable of nearly equivalent clarification.

Optimal dosing concentrations within systems were defined as the concentrations that accomplished the maximum degree of clarification per mg added. These concentrations were found to be: 200 mg/L protein from seed extract; 30 mg/L purified MO; 20 mg/L aluminum sulfate; and 50 mg/L ferric sulfate. Dosing with *M. oleifera* seed extract and purified MO resulted in reductions in turbidity of 84±5% and 76±1%, respectively. The addition of aluminum and ferric sulfates demonstrated a reduction in turbidity of 84±11% and 82±5%, respectively. Only a 1±6% reduction in turbidity was observed in controls that were not amended with a coagulant.

The purified MO was shown to have similar water clarification capabilities as the extracted *M. oleifera* seeds, but at one sixth the amount of protein. However, it should be noted that the protein concentration of the crude seed extract was calculated as the total amount of protein extracted from 1 g of seed into 100 mL of water. Several seed coagulant proteins have been identified in *M. oleifera*; thus, the total amount of coagulant protein in the seed extract relative to other exogenous proteins was unknown (Ali et al. 2010). Regardless, the purified MO could advantageously reduce the organic load going into a treatment system by about 6-fold to accomplish equivalent clarification.

MO Expression and Secretion in *B. subtilis*

After successfully demonstrating the optimized recombinant MO was active, the same construct (SEQ ID NO: 3) was subcloned into the expression vector pBE-S DNA and expressed in *B. subtilis*. Expression of this vector is under the control of the *B. subtilis*-derived aprE promoter, which controls production of subtilisin, a serine protease. The pBE-S DNA contains two origins of replication, allowing it to be shuttled between *E. coli* and the target *Bacillus* host.

The initial construction and propagation of the SP-MO library in *E. coli* is advantageous due to the relative ease of transformation as well as the production of high plasmid copy numbers, which are helpful for creating a large plasmid library required to screen the SP-MO clones. The pBE-S DNA expression vector has a multiple cloning site (MCS) for the MO gene insert, in addition to MluI and Eco52I restriction sites upstream of the MCS that allows the insertion of the random SP sequences (FIG. 3). Restriction sites NdeI and XbaI as the cloning sites for MO minimizes the extraneous sequence between the SP and the MO protein, which could negatively affect protein transport and coagulation activity. Additionally, RIK1285 is a protease deficient strain, which promotes protein persistence within the expression system (Murayama et al. 2004).

Signal peptides are short N-terminal amino acid sequences that act as targets for translocation machinery and transportation across the cytoplasmic membrane. Prokaryotic SP upstream of the protein to be secreted are on average 30 amino acids long and include three regions: a positively charged N domain, a hydrophobic core region, and a hydrophilic peptidase recognition site (Tjalsma et al. 2000 Brockmeier et al. 2006). All three regions play a role in the translocation process and are known to be protein specific, meaning SP action can vary significantly with different proteins.

Figure 6:
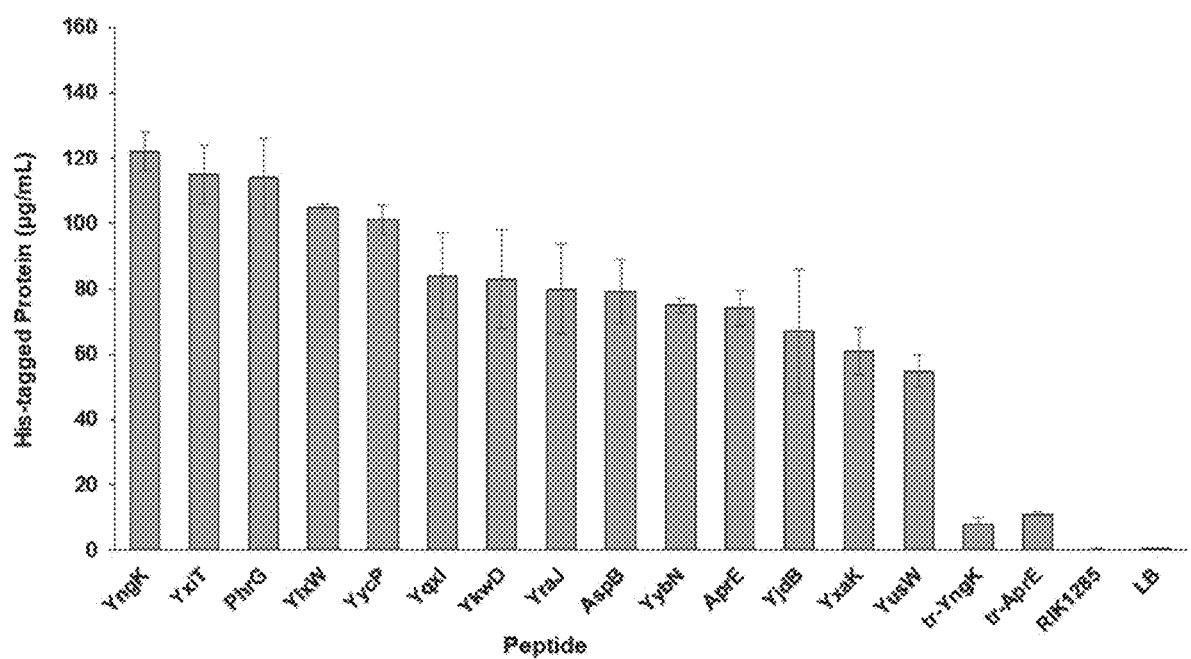
FIG. 6 is a graph presenting the ELISA quantitation of 6×His-tag protein in cell-free medium of selected pBE-S-SP-MO clones grown with LB. Error bars represent ±SD of 3 replicates.

Of the 440 clones screened, 14 were capable of producing epitope tagged proteins at concentrations ranging from 55 to 122 µg/mL (FIG. 6). The clones were sequenced and the SP were identified, and YngK (SEQ ID NO: 5) was found to secrete 122±6.0 µg/mL of tagged protein into the surrounding medium. The lowest secretor was YusW (SEQ ID NO: 1) at 55±5.0 µg/mL protein. No statistical differentiation was observed between YngK and the next 2 highest epitope secreting clones YxiT (SEQ ID NO: 6) and PhrG (SEQ ID NO: 7), which had extracellular 6×His tag concentrations of 115±9.1 µg/mL and 114±12.5 µg/mL, respectively. AprE (SEQ ID NO: 15), which is controlled by the native *B. subtilis*-derived subtilisin promoter (aprE promoter) secreted 74±5.4 µg/mL of protein.

Truncated SP YngK (tr-Yngk) (SEQ ID NO: 19) and AprE (tr-AprE) (SEQ ID NO: 20) were found to have significantly lower concentrations of tagged protein in the medium compared to the native SP, 8±1.9 µg/mL and 11±0.8 µg/mL, respectively. No tag was detected in the uninoculated controls (LB) (FIG. 6). Based on the ELISA screening, the clone containing MO fused to YngK SP (pBE-S-YngK-MO) (FIG. 4) was chosen for further study.

Specific SP characteristics were calculated from the 14 clones, and statistical analysis was performed to determine if any correlation existed between the amount of secreted protein and the peptide traits (Table 1). All the SP identified had D-scores>0.450 (0.460 to 0.893) and ranged in the number of amino acids residues from 21 to 41. Both truncated SP, as designed, had D-scores<0.450. All native SP had a net positive charge and pI>9.0 except YusW. The aliphatic index ranged from 94.2 to 139.5, GRAVY from 0.513 to 1.567, and hydrophobicity from 52 to 74%. Linear regression analysis of the peptide characteristics produced p-values all in excess of 0.05 and $R^2$ values of <0.3. Stepwise variable selection resulted in no variables being selected. Furthermore, ANOVA showed no positive results in the analysis.

TABLE 1

Characteristics of signal peptides identified by ELISA screening. The SP are listed in descending order from high to low concentration in the cell-free medium.

| SP | Amino acid sequence | SEQ ID NO | D-score[a] | Charge[b] | pI[c] | Aliphatic Index[c] | GRAVY[c] | Hydrophobicity (%)[d] |
|---|---|---|---|---|---|---|---|---|
| YngK | MKVCQKSIVRFLVSLIIGTFVISVPFMANA | 5 | 0.716 | +3 | 10.1 | 133.0 | 1.350 | 63 |
| YxiT | MKWNNMLKAAGIAVLLFSVFAYAAPSLKAVQA | 6 | 0.618 | +3 | 10.0 | 113.1 | 0.878 | 69 |
| PhrG | MKRFLIGAGVAAVILSGWFIA | 7 | 0.464 | +2 | 11.0 | 139.5 | 1.567 | 71 |
| YlxW | MRGKSAVLLSLIMLIAGFLISFSFQMTKENNKSAA | 8 | 0.519 | +3 | 10.3 | 108.9 | 0.637 | 54 |
| YycP | MKKWMITIAMLILAGIALFVFISPLKS | 9 | 0.512 | +3 | 10.3 | 151.9 | 1.544 | 74 |
| Yqxl | MFKKLLLATSALTFSLSLVLPLDGHAKA | 10 | 0.668 | +2 | 9.7 | 136.1 | 0.896 | 61 |
| YkwD | MKKAFILSAAAAVGLFTFGGVQQASA | 11 | 0.775 | +2 | 10.0 | 94.2 | 0.965 | 62 |
| YraJ | MTLTKLKMLSMLTVMIASLFIFSSQALA | 12 | 0.741 | +2 | 10.0 | 132.5 | 1.357 | 64 |
| AspB | MKLAKRVSALTPSTTLAITAKA | 13 | 0.603 | +4 | 11.3 | 106.8 | 0.400 | 55 |
| YbbN | MNKFLKSNFRFLLAAALGISLLASSNFIKA | 14 | 0.657 | +4 | 11.3 | 120.7 | 0.787 | 60 |
| AprE | MRSKKLWISLLFALTLIFTMAFSNMSVQA | 15 | 0.692 | +3 | 11.1 | 114.5 | 0.928 | 62 |
| YjdB | MNFKKTVVSALSISALALSVSGVASA | 16 | 0.893 | +2 | 10.0 | 123.9 | 1.123 | 58 |
| YxaK | MVKSFRMKALIAGAAVAAAVSAGAVSDVPAAKVLQPTAAYA | 17 | 0.577 | +3 | 10.0 | 105.1 | 0.915 | 68 |
| YusW | MHLIRAAGAVCLAVVLIAGCRFNEDQHQAEG | 18 | 0.460 | −1 | 6.5 | 110.3 | 0.513 | 52 |
| tr-YngK | MIIGTFVISVPFMANA | 19 | 0.431 | 0 | 5.5 | 121.9 | 1.744 | 69 |
| tAprE | MLIFTMAFSNMSAQA | 20 | 0.411 | 0 | 5.5 | 72.0 | 1.047 | 67 |

[a] Signal peptide (SP) D-scores were calculated using SignalP 4.1.
[b] Net charge calculated by Protein Calculator v3.4 at neutral pH.
[c] Values were calculated using ProParam: isoelectric point (pI); grand average of hydropathicity (GRAVY).
[d] Hydrophobicity was calculated by dividing the total number of hydrophobic amino acids by the total number of residues.

Previous studies have suggested that effective SP protein combinations can only be determined empirically due to the complexity of the transport system and diversity of target proteins (Hemmerich et al. 2016). The statistical analysis supported this contention, in that no significant correlation could be found between the amount of secreted protein and any of the parameters listed in Table 1. This further illustrates the usefulness of an immunological approach for screening large libraries for efficient protein secreting clones.

Figure 7A:
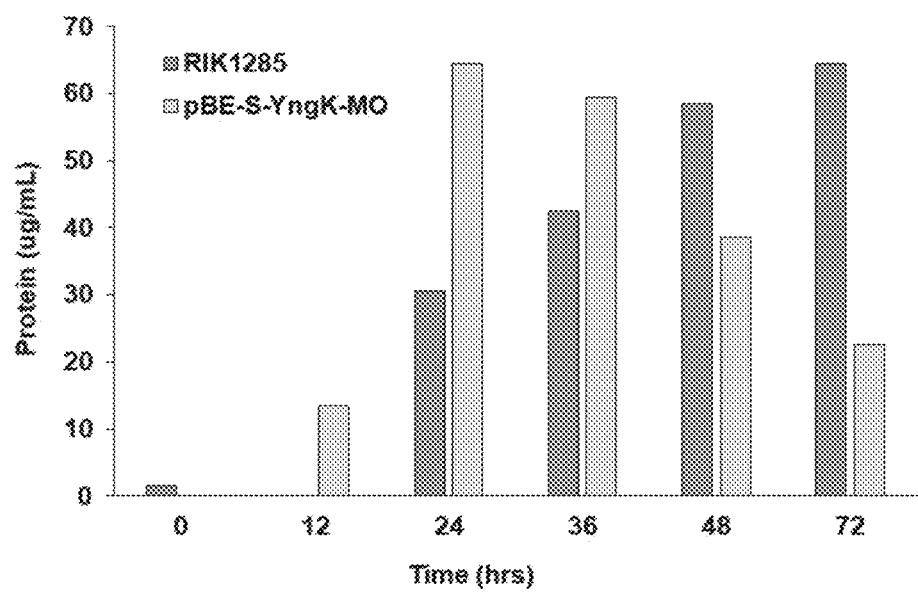
FIGS. 7A-7C show exogenous protein concentration and visible cell flocculation in 100 mL cultures of pBE-S-YngK-MO and untransformed *Bacillus subtilis* (RIK1285).
Figure 7B:
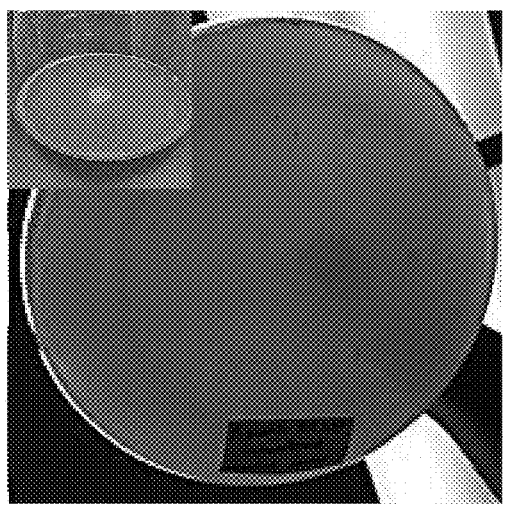
Figure 7C:
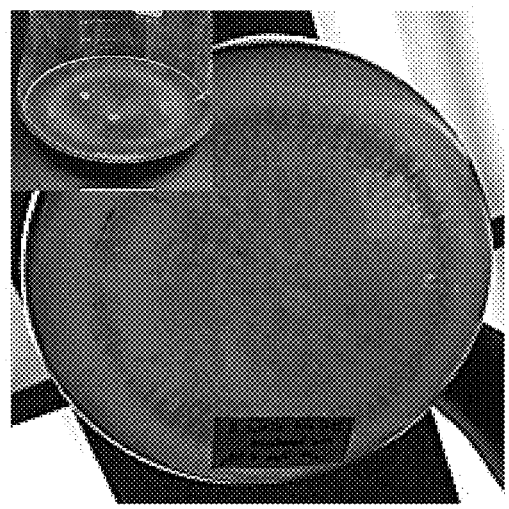

When grown on LB, pBE-S-YngK-MO exhibited an initial increase in exogenous protein concentration when compared to untransformed RIK1285 and was capable of precipitating cells out of solution (FIG. 7A-7C). After a 24 hr incubation period, the pBE-S-YngK-MO strain containing the MO gene produced 2-fold more exogenous protein than the RIK1285 wild type strain (FIG. 7A). However, protein concentrations slowly decreased over a 72 hr incubation period in the culture containing pBE-S-YngK-MO, whereas in the RIK1285 containing culture, protein steadily increased. After 72 hrs, the cell-free medium protein concentration in the untransformed culture was nearly equal to the strain harboring the MO gene after 24 hrs incubation. However, the total protein in the cell-free medium in the transformed strain decreased nearly 2-fold after an additional 48 hrs incubation. Furthermore, when the pBE-S-YngK-MO culture was allowed to rest without shaking, a 70% to 80% reduction in turbidity in the MO gene containing culture was observed, and flocked cells could clearly be seen with the naked eye (FIGS. 7B and 7C).

Figure 8A:
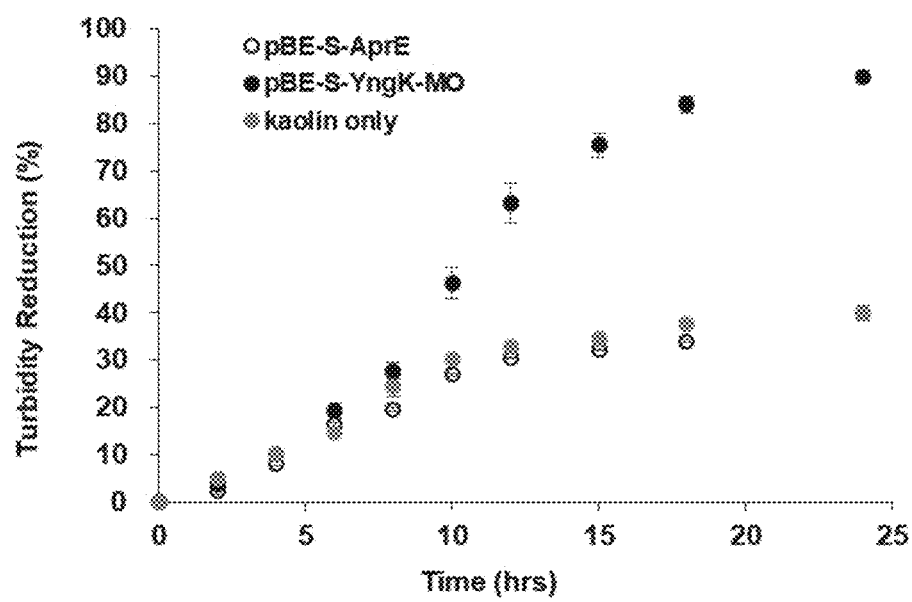
FIGS. 8A-8B show the clarification of turbid water using cell-free medium from pBE-S-YngK-MO.
Figure 8B:
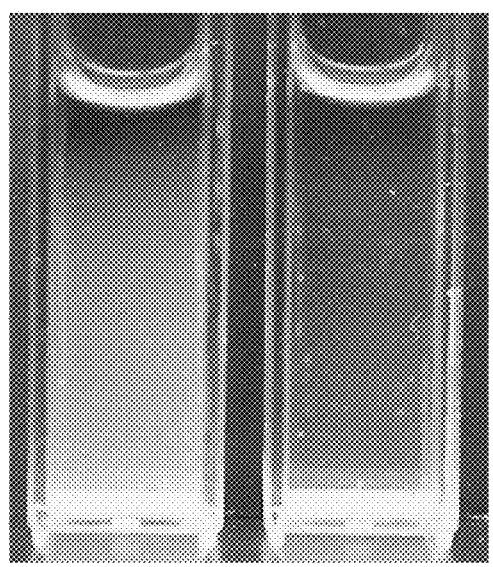

Cell-free media of pBE-S-AprE (no MO gene) and pBE-S-YngK-MO grown on LB were tested for their ability to clarify water. The total amount of protein added to the assays was 15 kg/mL. After a 24 hr settling period, the media from pBE-S-YngK-MO reduced turbidity by about 90%, while pBE-S-AprE did not reduce turbidity relative to the control, containing no cell-free medium (FIG. 8A). Turbidity reduction in the culture containing pBE-S-YngK-MO was significantly greater than the pBE-S-AprE and cell-free medium controls after 10 hrs and continued to increase over the course of the experiment. Essentially no variance in turbidity was observed between the uninoculated control and pBE-S-AprE. After 24 hrs, the medium from pBE S-YngK-MO showed a 50% greater reduction in turbidity compared to the control and pBE-S-AprE, which was clearly visible by the naked eye (FIG. 8B).

To confirm the presence of 6×His epitope tagged heterologous protein within the cell-free medium of pBE-S-YngK-MO, immunoblot analysis was performed on an affinity chromatography purified sample. The purified fraction was analyzed by SDS-PAGE (FIG. 9A), and while no band was observed in pBE-S-AprE inoculated culture (lane 1), a band was clearly visible in pBE-S-YngK-MO inoculated culture (lane 5). This band had an approximate molecular weight of 8.4 kDa, the expected weight of MO without YngK. Proteins within the gel were transferred to a PVDF membrane and probed for the presence of a 6×His tag via immunoblotting. Western blotting with anti-6×His-tag IgG primary antibody (FIG. 9B) confirmed the presence of the 6×His within the purified band having the approximate calculated molecular weight as the target recombinant coagulant protein (lane 10). No affinity was detected in the pBE-S-AprE control (lane 6).

MO Expression and Secretion in *B. subtilis* when Grown on Simulated Wastewater

To determine the ability of pBE-S-YngK-MO to utilize various substrates (other than LB) to secrete recombinant protein, an ELISA array was performed. Mixtures of synthetic black water (BW) with various concentrations of casein, tryptone, and milk powder were evaluated for their ability to support the secretion of 6×His-tagged MO (FIG. 10). Synthetic black water containing 0.5% and 1% tryptone resulted in the greatest amount of 6×His-tagged MO protein at 57.6±1.7 µg/mL and 65.0±2.0 µg/mL, respectively. When grown on tryptone only (no black water) 5.9±0.3 µg/mL of protein was secreted. The amount of 6×His-tagged MO protein decreased from 26.8±0.4 µg/mL to 9.3±0.7 µg/mL as the concentration of casein increased from 0.25% to 1% in the synthetic black water. The casein only culture produced 5.3±2.1 µg/mL of tagged protein in the medium. When pBE-S-YngK-MO was grown with synthetic black water and milk protein, the extracellular 6×His-tagged MO protein concentration increased from 3.2±1.4 µg/mL to 28.0±2.0 µg/mL, and no tagged protein was detected in cell-free medium without the addition of black water. The uninoculated LB and BW controls produced no observable growth (FIG. 10).

The cultures grown in black water supplemented with 0.5% tryptone produced the highest viable biomass, with 3.09E+08±3.26E+07 cells/mL. The biomass decreased from 1.38E+08±4.83E+07 to 6.79E+07±3.09E+07 cells/mL in the 1% tryptone cultures in the absence of black water. Cell numbers ranged from 1.74E+08±3.19E+07 to 2.12E+08±5.09E+07 cells/mL in the black water amended with casein and only 8.70E+05±2.85E+05 in the cultures without black water. Viable cell numbers ranged from 2.88E+06±1.50E+05 to 1.41E+08±7.75E+07 cells/mL in the black water amended with milk powder and only 1.00E+06±1.33E+05 in the cultures without black water (FIG. 10).

Figure 11A:
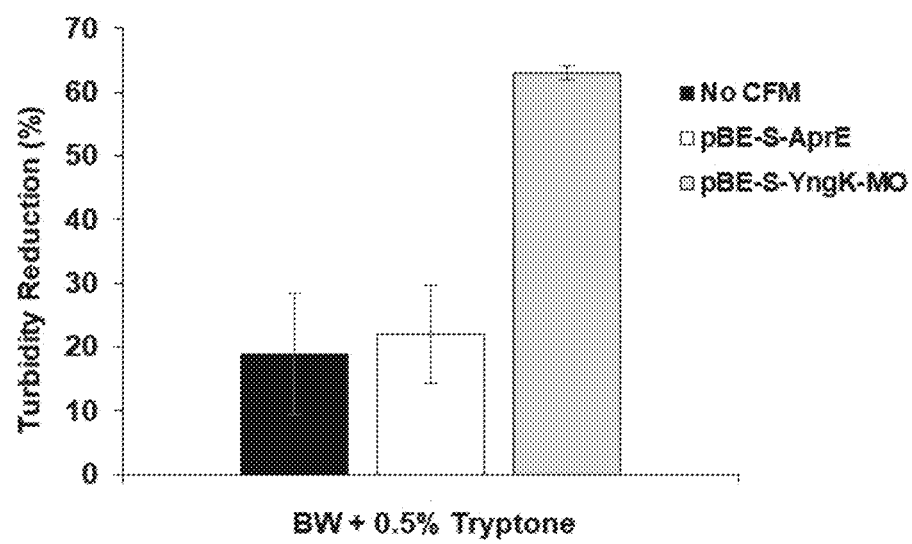
FIGS. 11A-11B show the clarification of turbid water using cell-free medium from pBE-S-YngK-MO grown with BW+0.5% Tryptone.
Figure 11B:
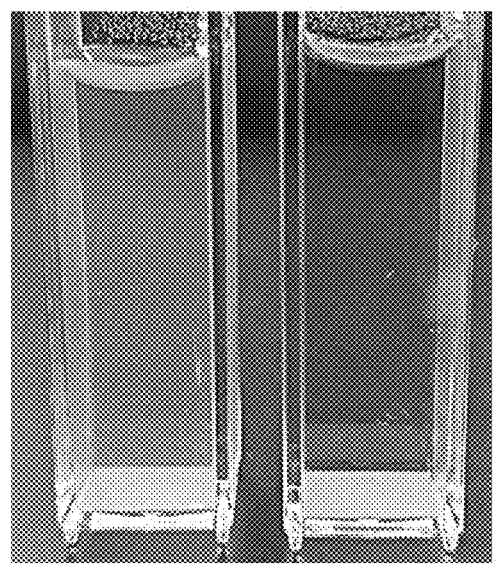

Cell-free medium from pBE-S-YngK-MO grown on synthetic black water containing 0.5% tryptone reduced turbidity more than 2-fold compared to controls over a 48 hr settling period (FIG. 11A). Controls containing no cell-free medium and cell-free medium from the MO deficient strain pBE-S-AprE reduced turbidity 19%±10% and 22%±8%, respectively. In comparison, cell-free medium from pBE-S-YngK-MO reduced turbidity by 63%±1%. Furthermore, water clarification mediated by cell-free medium from the pBE-S-YngK-MO strain could clearly be seen by the naked eye (FIG. 11B).

REFERENCES

Ali E N, Muyibi S A, Salleh H M, Alam M Z, Salleh M R M (2010) Production of natural coagulant from *Moringa oleifera* for application in treatment of low turbidity water. J Wat Resour Prot 2:259-266.

Bradford M M (1976) A rapid and sensitive method for the quantitation of microgram quantities of protein utilizing the principle of protein-dye binding. Anal Biochem 72:248-254.

Broin M, Santaella C, Cuine S, Kokou K, Peltier G, Joët T (2002) Flocculent activity of a recombinant protein from *Moringa oleifera* Lam. seeds. Appl Microbiol Biotechnol 60:114-119.

Brockmeier U, Caspers M, Freudl R, Jockwer A, Noll T, Eggert T (2006) Systematic screening of all signal peptides from *Bacillus subtilis*: A powerful strategy in optimizing heterologous protein secretion in Gram-positive bacteria. J Mol Biol 362:393-402.

Cazcarro I, López-Morales C, Duchin F (2016) The global economic costs of the need to treat polluted water. Econ Syst Res 28:295-314.

De Souza Fermino L, De castro Silva Pedrangelo A, De Matos Silva P K, De Azevedo R E C, Yamaguchi N U, Ribeiro R M (2017) Water treatment with conventional and alternative coagulants. Chemical Engineering Transactions 57:1189-1194.

Fu L L, Xu Z R, Li W F, Shuai J B, Lu P, Hu C X (2007) Protein secretion pathways in *Bacillus subtilis*: implications for optimization of heterologous protein secretion. Biotechnol Adv 25:1-12.

Gasteiger E, Hoogland C, Gattiker A, Duvaud S, Wilkins M R, Appel R D, Bairoch A (2005) Protein Identification and Analysis Tools on the ExPASy Server. In: John M. Walker (ed): The Proteomics Protocols Handbook, Humana Press pp. 571-607.

Ghebremichael K A, Gunaratna K R, Henriksson H, Brumer H, Dalhammar G (2005) A simple purification and activity assay of the coagulant protein from *Moringa oleifera* seed. Wat Res 39:2338-2344.

Hemmerich J, Rohe P, Kleine B, Jurischka S, Wiechert W, Freudl R, Oldiges M (2016) Use of a Sec signal peptide library from *Bacillus subtilis* for the optimization of cutinase secretion in *Corynebacterium glutatmicum*. Microb Cell Fact 15:208-219.

Kansal S K, Kumari A (2014) Potential of *M. oleifera* for the treatment of water and wastewater. Chem Rev 114:4993-5010.

Murayama R, Akanuma G. Mankino Y, Nanamiya H, Kawamura F (2004) Spontaneous transformation and use for genetic mapping in *Bacillus subtilis*. Biosci Biotechnol Biochem 68:1672-1680.

Muyibi S A, Evison L M (1995) Optimizing physical parameters affecting coagulation of turbid water with *Moringa oleifera* seeds. Wat Res 29:289-2695.

Narasiah K S, Vogel A, Kramadhati N (2002) Coagulation of turbid waters using *Moringa oleifera* seeds from two distinct sources. Wat Sci Technol 2:83-88.

Ndabigengesere A, Subba K, Talbot B G (1995) Active agents and mechanism of coagulation of turbid waters using *Moringa oleifera*. Wat Res 29:703-710.

Nopens I, Capalozza C, Vanrolleghem P A (2001) Stability analysis of a synthetic municipal wastewater. Technical report, Department of Applied Mathematics, Biometrics and Process Control. Tech Universiteit Gent.

Okuda T, Baes A U, Nishijima W, Okadam M (2001) Isolation and characterization of coagulant extracted from *Moringa oleifera* seed by salt solution. Wat Res 35:405-410.

Olsona M (2017) *Moringa* frequently asked questions. Acta Horticulturae 1158:19-32.

Pavankumar A R, Nor'en J, Singh L, Gowda N K C (2014) Scaling-up the production of recombinant *Moringa oleifera* coagulant protein for large-scale water treatment applications. RCS Adv 4:7136-7141.

Petersen T N, Brunak S, von Heijne G, Nielsen H (2011) SignalP 4.0: discriminating signal peptides from transmembrane regions. Nat Methods 8:785-786.

Poumaye N, Mabingui J, Lutgen P, Bigan M (2012) Contribution to the clarification of surface water from the *Moringa oleifera*: Case Ms Poko River to Bangui, Central African Republic. Chem Eng Res Des 90:2346-2352.

Rajasulochana P, Preethy V (2016) Comparison on efficiency of various techniques in treatment of waste and sewage water—a comprehensive review. Resour Eff Technol 2:175-184.

Ramachandran C, Peter K V, Gopalakrishnan P K (1980) Drumstick (*Moringa oleifera*): A multipurpose Indian vegetable. Economic Botany 34:276-283.

Ramavandi B (2014) Treatment of water turbidity and bacteria by using a coagulant extracted from *Plantago ovata*. Water Resour Ind 6:36-50.

Ravani A, Prasad R V, Gajeral R R, Joshi D C (2017) Potentiality of *Moringa oleifera* for food and nutritional security. Ag Rev 38:228-232.

Sambrook J, Russell D W (2001). Molecular cloning: a laboratory manual. 3rd ed. Cold Spring Harbor: Cold Spring Harbor Laboratory Press.

Schallmey M, Singh A, Ward O P (2004) Developments in the use of *Bacillus* species for industrial production. Can J Microbiol 50:1-17.

Schumann W (2007) Production of recombinant proteins in *Bacillus subtilis*. Adv Appl Microbiol 62:137-189.

Suarez M, Entenza J M, Doerries C, Meyer E, Bourquin L, Sutherland J, Marison I, Moreillon P, Mennod N (2002) Expression of a plant-derived peptide harboring water-cleaning and antimicrobial activities. Biotech Bioeng 81:13-20.

Tjalsma H, Bolhuis A, Jongbloed J D H, Bron S, Van Dijl J M (2000) Signal peptide-dependent protein transport in *Bacillus subtilis*: a genome-based survey of the secretome. Microbiol Mol Biol Rev 64:515-547.

United Nations World Water Assessment Programme (2017) The United Nations World Water Development Report 2017—Wastewater: The Untapped Resource. Paris, France: UNESCO.

Yongabi K A (2010) Biocoagulants for water and waste water purification a review. Int Rev Chem Eng 2:444-458.

What is claimed is:

1. A method for treating contaminated drinking water, comprising contacting the water with an effective amount of a composition, said composition comprising:
   a recombinant *Moringa oleifera* MO protein produced and secreted by *Bacillus* and having coagulation or flocculation activity,
   wherein said MO protein produced and secreted by *Bacillus* is fused or linked to a *Bacillus* signal peptide (SP), and wherein;
   said signal peptide (SP is at least one selected from the group consisting of: YngK (SEQ ID NO: 5), YxiT (SEQ ID NO: 6), PhrG (SEQ ID NO: 7), YklxW (SEQ ID NO: 8), YycP (SEQ ID NO: 9), YqxI (SEQ ID NO: 10), YkwD (SEQ ID NO: 11), YraJ (SEQ ID NO: 12), AspB (SEQ ID NO: 13), YybN (SEQ ID NO: 14), AprE (SEQ ID NO: 15), YjdB (SEQ ID NO: 16), YxaK (SEQ ID NO: 17), and YusW (SEQ ID NO: 18).

2. The method of claim 1, comprising: contacting the composition to the contaminated drinking water to obtain partially purified water comprising coagulated or flocculated matter; removing at least part of the coagulated or flocculated matter from the partially purified water by sedimentation, filtration, decanting, flotation, or a combination thereof, to obtain purified water having at least a 90% reduction in turbidity.

3. The method of claim 1, for the batchwise purification and clarification of a relatively small predetermined volume of contaminated drinking water, comprising: adding an effective amount of the composition in unit dosage form to the predetermined volume of contaminated water; dispersing the composition in the water to coagulate and flocculate suspended solid impurities therein; allowing the dispersed water to stand; and filtering the water to remove said impurities and to obtain purified water suitable for human consumption having at least a 90% reduction in turbidity.

4. The method of claim 1, wherein the predetermined volume of water is in a range of 0.1 to 100 liters.

5. The method of claim 1, wherein the predetermined volume of water is in a range of 0.5 to 2 liters.

6. The method of claim 1, wherein the *Bacillus* cells comprise *B. subtilis* cells.

7. The method of claim 1, wherein said signal peptide (SP) is YngK (SEQ ID NO: 5).

* * * * *

SEQUENCE LISTING

<160> NUMBER OF SEQ ID NOS: 31

<210> SEQ ID NO 1
<211> LENGTH: 183
<212> TYPE: DNA
<213> ORGANISM: Moringa oleifera
<220> FEATURE:
<221> NAME/KEY: CDS
<222> LOCATION: (1)..(183)
<223> OTHER INFORMATION: MO gene: NCBI Accession No. AJ345072

<400> SEQUENCE: 1

```
cag gga cct ggt cgg cag ccg gac ttt cag cgt tgc tgc caa cag ctg      48
Gln Gly Pro Gly Arg Gln Pro Asp Phe Gln Arg Cys Cys Gln Gln Leu
 1               5                  10                  15
```

```
cgg aac ata tct cct cct tgc agg tgc cca tca ctc agg caa gca gta    96
Arg Asn Ile Ser Pro Pro Cys Arg Cys Pro Ser Leu Arg Gln Ala Val
         20                  25                  30 cag ttg aca cac cag cag cag gga cag gtg ggt cct cag cag gta agg   144
Gln Leu Thr His Gln Gln Gln Gly Gln Val Gly Pro Gln Gln Val Arg
     35                  40                  45 cag atg tac cga gtg gca tcc aat ata cct agc acc taa               183
Gln Met Tyr Arg Val Ala Ser Asn Ile Pro Ser Thr
 50                  55                  60

<210> SEQ ID NO 2
<211> LENGTH: 60
<212> TYPE: PRT
<213> ORGANISM: Moringa oleifera

<400> SEQUENCE: 2

Gln Gly Pro Gly Arg Gln Pro Asp Phe Gln Arg Cys Cys Gln Gln Leu
 1               5                  10                  15

Arg Asn Ile Ser Pro Pro Cys Arg Cys Pro Ser Leu Arg Gln Ala Val
             20                  25                  30

Gln Leu Thr His Gln Gln Gln Gly Gln Val Gly Pro Gln Gln Val Arg
         35                  40                  45

Gln Met Tyr Arg Val Ala Ser Asn Ile Pro Ser Thr
     50                  55                  60

<210> SEQ ID NO 3
<211> LENGTH: 183
<212> TYPE: DNA
<213> ORGANISM: Artificial Sequence
<220> FEATURE:
<223> OTHER INFORMATION: MO gene after codon optimization
<220> FEATURE:
<221> NAME/KEY: CDS
<222> LOCATION: (1)..(183)

<400> SEQUENCE: 3 caa ggt ccg ggt cgc caa ccg gat ttt caa cgc tgc tgc caa caa ctg    48
Gln Gly Pro Gly Arg Gln Pro Asp Phe Gln Arg Cys Cys Gln Gln Leu
 1               5                  10                  15 cgt aac att agc ccg ccg tgc cgc tgc ccg agc ctg cgc caa gcg gtg    96
Arg Asn Ile Ser Pro Pro Cys Arg Cys Pro Ser Leu Arg Gln Ala Val
             20                  25                  30 cag ctg acc cac cag caa cag ggt caa gtt ggt ccg cag caa gtt cgt   144
Gln Leu Thr His Gln Gln Gln Gly Gln Val Gly Pro Gln Gln Val Arg
         35                  40                  45 caa atg tat cgt gtg gcg agc aat atc ccg agc acc taa               183
Gln Met Tyr Arg Val Ala Ser Asn Ile Pro Ser Thr
     50                  55                  60

<210> SEQ ID NO 4
<211> LENGTH: 60
<212> TYPE: PRT
<213> ORGANISM: Artificial Sequence
<220> FEATURE:
<223> OTHER INFORMATION: Synthetic Construct

<400> SEQUENCE: 4

Gln Gly Pro Gly Arg Gln Pro Asp Phe Gln Arg Cys Cys Gln Gln Leu
 1               5                  10                  15

Arg Asn Ile Ser Pro Pro Cys Arg Cys Pro Ser Leu Arg Gln Ala Val
             20                  25                  30

Gln Leu Thr His Gln Gln Gln Gly Gln Val Gly Pro Gln Gln Val Arg
         35                  40                  45
```

```
Gln Met Tyr Arg Val Ala Ser Asn Ile Pro Ser Thr
    50                  55                  60
```

<210> SEQ ID NO 5
<211> LENGTH: 30
<212> TYPE: PRT
<213> ORGANISM: Bacillus subtilis
<220> FEATURE:
<221> NAME/KEY: SIGNAL
<222> LOCATION: (1)..(30)
<223> OTHER INFORMATION: YngK

<400> SEQUENCE: 5

```
Met Lys Val Cys Gln Lys Ser Ile Val Arg Phe Leu Val Ser Leu Ile
1               5                   10                  15

Ile Gly Thr Phe Val Ile Ser Val Pro Phe Met Ala Asn Ala
            20                  25                  30
```

<210> SEQ ID NO 6
<211> LENGTH: 32
<212> TYPE: PRT
<213> ORGANISM: Bacillus subtilis
<220> FEATURE:
<221> NAME/KEY: SIGNAL
<222> LOCATION: (1)..(32)
<223> OTHER INFORMATION: YxiT

<400> SEQUENCE: 6

```
Met Lys Trp Asn Asn Met Leu Lys Ala Ala Gly Ile Ala Val Leu Leu
1               5                   10                  15

Phe Ser Val Phe Ala Tyr Ala Ala Pro Ser Leu Lys Ala Val Gln Ala
            20                  25                  30
```

<210> SEQ ID NO 7
<211> LENGTH: 21
<212> TYPE: PRT
<213> ORGANISM: Bacillus subtilis
<220> FEATURE:
<221> NAME/KEY: SIGNAL
<222> LOCATION: (1)..(21)
<223> OTHER INFORMATION: PhrG

<400> SEQUENCE: 7

```
Met Lys Arg Phe Leu Ile Gly Ala Gly Val Ala Ala Val Ile Leu Ser
1               5                   10                  15

Gly Trp Phe Ile Ala
            20
```

<210> SEQ ID NO 8
<211> LENGTH: 35
<212> TYPE: PRT
<213> ORGANISM: Bacillus subtilis
<220> FEATURE:
<221> NAME/KEY: SIGNAL
<222> LOCATION: (1)..(35)
<223> OTHER INFORMATION: YlxW

<400> SEQUENCE: 8

```
Met Arg Gly Lys Ser Ala Val Leu Leu Ser Leu Ile Met Leu Ile Ala
1               5                   10                  15

Gly Phe Leu Ile Ser Phe Ser Phe Gln Met Thr Lys Glu Asn Asn Lys
            20                  25                  30

Ser Ala Ala
        35
```

```
<210> SEQ ID NO 9
<211> LENGTH: 27
<212> TYPE: PRT
<213> ORGANISM: Bacillus subtilis
<220> FEATURE:
<221> NAME/KEY: SIGNAL
<222> LOCATION: (1)..(27)
<223> OTHER INFORMATION: YycP

<400> SEQUENCE: 9

Met Lys Lys Trp Met Ile Thr Ile Ala Met Leu Ile Leu Ala Gly Ile
1               5                   10                  15

Ala Leu Phe Val Phe Ile Ser Pro Leu Lys Ser
            20                  25

<210> SEQ ID NO 10
<211> LENGTH: 28
<212> TYPE: PRT
<213> ORGANISM: Bacillus subtilis
<220> FEATURE:
<221> NAME/KEY: SIGNAL
<222> LOCATION: (1)..(28)
<223> OTHER INFORMATION: YqxI
<220> FEATURE:
<221> NAME/KEY: SIGNAL
<222> LOCATION: (2)..(28)
<223> OTHER INFORMATION: YqxI

<400> SEQUENCE: 10

Met Phe Lys Lys Leu Leu Leu Ala Thr Ser Ala Leu Thr Phe Ser Leu
1               5                   10                  15

Ser Leu Val Leu Pro Leu Asp Gly His Ala Lys Ala
            20                  25

<210> SEQ ID NO 11
<211> LENGTH: 26
<212> TYPE: PRT
<213> ORGANISM: Bacillus subtilis
<220> FEATURE:
<221> NAME/KEY: SIGNAL
<222> LOCATION: (1)..(26)
<223> OTHER INFORMATION: YkwD

<400> SEQUENCE: 11

Met Lys Lys Ala Phe Ile Leu Ser Ala Ala Ala Val Gly Leu Phe
1               5                   10                  15

Thr Phe Gly Gly Val Gln Gln Ala Ser Ala
            20                  25

<210> SEQ ID NO 12
<211> LENGTH: 28
<212> TYPE: PRT
<213> ORGANISM: Bacillus subtilis
<220> FEATURE:
<221> NAME/KEY: SIGNAL
<222> LOCATION: (1)..(28)
<223> OTHER INFORMATION: YraJ

<400> SEQUENCE: 12

Met Thr Leu Thr Lys Leu Lys Met Leu Ser Met Leu Thr Val Met Ile
1               5                   10                  15

Ala Ser Leu Phe Ile Phe Ser Ser Gln Ala Leu Ala
            20                  25

<210> SEQ ID NO 13
<211> LENGTH: 22
```

```
<212> TYPE: PRT
<213> ORGANISM: Bacillus subtilis
<220> FEATURE:
<221> NAME/KEY: SIGNAL
<222> LOCATION: (1)..(22)
<223> OTHER INFORMATION: AspB

<400> SEQUENCE: 13

Met Lys Leu Ala Lys Arg Val Ser Ala Leu Thr Pro Ser Thr Thr Leu
1               5                   10                  15

Ala Ile Thr Ala Lys Ala
            20

<210> SEQ ID NO 14
<211> LENGTH: 30
<212> TYPE: PRT
<213> ORGANISM: Bacillus subtilis
<220> FEATURE:
<221> NAME/KEY: SIGNAL
<222> LOCATION: (1)..(30)
<223> OTHER INFORMATION: YybN

<400> SEQUENCE: 14

Met Asn Lys Phe Leu Lys Ser Asn Phe Arg Phe Leu Leu Ala Ala Ala
1               5                   10                  15

Leu Gly Ile Ser Leu Leu Ala Ser Ser Asn Phe Ile Lys Ala
            20                  25                  30

<210> SEQ ID NO 15
<211> LENGTH: 29
<212> TYPE: PRT
<213> ORGANISM: Bacillus subtilis
<220> FEATURE:
<221> NAME/KEY: SIGNAL
<222> LOCATION: (1)..(29)
<223> OTHER INFORMATION: AprE

<400> SEQUENCE: 15

Met Arg Ser Lys Lys Leu Trp Ile Ser Leu Leu Phe Ala Leu Thr Leu
1               5                   10                  15

Ile Phe Thr Met Ala Phe Ser Asn Met Ser Val Gln Ala
            20                  25

<210> SEQ ID NO 16
<211> LENGTH: 26
<212> TYPE: PRT
<213> ORGANISM: Bacillus subtilis
<220> FEATURE:
<221> NAME/KEY: SIGNAL
<222> LOCATION: (1)..(26)
<223> OTHER INFORMATION: YjdB

<400> SEQUENCE: 16

Met Asn Phe Lys Lys Thr Val Val Ser Ala Leu Ser Ile Ser Ala Leu
1               5                   10                  15

Ala Leu Ser Val Ser Gly Val Ala Ser Ala
            20                  25

<210> SEQ ID NO 17
<211> LENGTH: 41
<212> TYPE: PRT
<213> ORGANISM: Bacillus subtilis
<220> FEATURE:
<221> NAME/KEY: SIGNAL
<222> LOCATION: (1)..(41)
<223> OTHER INFORMATION: YxaK
```

<400> SEQUENCE: 17

Met Val Lys Ser Phe Arg Met Lys Ala Leu Ile Ala Gly Ala Ala Val
1               5                   10                  15

Ala Ala Ala Val Ser Ala Gly Ala Val Ser Asp Val Pro Ala Ala Lys
                20                  25                  30

Val Leu Gln Pro Thr Ala Ala Tyr Ala
        35                  40

<210> SEQ ID NO 18
<211> LENGTH: 31
<212> TYPE: PRT
<213> ORGANISM: Bacillus subtilis
<220> FEATURE:
<221> NAME/KEY: SIGNAL
<222> LOCATION: (1)..(31)
<223> OTHER INFORMATION: YusW

<400> SEQUENCE: 18

Met His Leu Ile Arg Ala Ala Gly Ala Val Cys Leu Ala Val Val Leu
1               5                   10                  15

Ile Ala Gly Cys Arg Phe Asn Glu Asp Gln His Gln Ala Glu Gly
                20                  25                  30

<210> SEQ ID NO 19
<211> LENGTH: 16
<212> TYPE: PRT
<213> ORGANISM: Artificial Sequence
<220> FEATURE:
<223> OTHER INFORMATION: tr-YngK

<400> SEQUENCE: 19

Met Ile Ile Gly Thr Phe Val Ile Ser Val Pro Phe Met Ala Asn Ala
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: tr-AprE

<400> SEQUENCE: 20

Met Leu Ile Phe Thr Met Ala Phe Ser Asn Met Ser Ala Gln Ala
1               5                   10                  15

<210> SEQ ID NO 21
<211> LENGTH: 315
<212> TYPE: DNA
<213> ORGANISM: Artificial Sequence
<220> FEATURE:
<223> OTHER INFORMATION: pBE-S-YngK-MO

<400> SEQUENCE: 21
atgaaggttt gccaaaagtc gattgtccgt ttccttgtca gcttgatcat cggaacgttt     60
gtcatttccg ttccgtttat ggccaatgcg gcggccggtg cacatatgca aggtccgggt    120
cgccaaccgg attttcaacg ctgctgccaa caactgcgta acattagccc gccgtgccgc    180
tgcccgagcc tgcgcaaagc ggtgcagctg acccaccagc aacagggtca agttggtccg    240
cagcaagttc gtcaaatgta tcgtgtggcg agcaatatcc cgagcacctc tagacatcac    300
catcatcacc actaa                                                     315

<210> SEQ ID NO 22

<211> LENGTH: 273
<212> TYPE: DNA
<213> ORGANISM: Artificial Sequence
<220> FEATURE:
<223> OTHER INFORMATION: pBE-S-trYngK-MO (truncated YngK)

<400> SEQUENCE: 22

| | | |
|---|---|---|
| atgatcatcg gaacgtttgt catttccgtt ccgtttatgg ccaatgcggc ggccggtgca | 60 |
| catatgcaag gtccgggtcg ccaaccggat tttcaacgct gctgccaaca actgcgtaac | 120 |
| attagcccgc cgtgccgctg cccgagcctg cgccaagcgg tgcagctgac ccaccagcaa | 180 |
| cagggtcaag ttggtccgca gcaagttcgt caaatgtatc gtgtggcgag caatatcccg | 240 |
| agcacctcta gacatcacca tcatcaccac taa | 273 |

<210> SEQ ID NO 23
<211> LENGTH: 270
<212> TYPE: DNA
<213> ORGANISM: Artificial Sequence
<220> FEATURE:
<223> OTHER INFORMATION: pBE-S-AprE-MO

<400> SEQUENCE: 23

| | | |
|---|---|---|
| gtgttaatct ttacgatggc gttcagcaac atgtctgcgc aggctgcggc cggtgcacat | 60 |
| atgcaaggtc cgggtcgcca accggatttc aacgctgct gccaacaact gcgtaacatt | 120 |
| agcccgccgt gccgctgccc gagcctgcgc aagcggtgc agctgaccca ccagcaacag | 180 |
| ggtcaagtgg gtccgcagca agttcgtcaa atgtatcgtg tggcgagcaa tatcccgagc | 240 |
| acctctagac atcaccatca tcaccactaa | 270 |

<210> SEQ ID NO 24
<211> LENGTH: 270
<212> TYPE: DNA
<213> ORGANISM: Artificial Sequence
<220> FEATURE:
<223> OTHER INFORMATION: pBE-S-trAprE-MO (truncated AprE)

<400> SEQUENCE: 24

| | | |
|---|---|---|
| gtgttaatct ttacgatggc gttcagcaac atgtctgcgc aggctgcggc cggtgcacat | 60 |
| atgcaaggtc cgggtcgcca accggatttc aacgctgct gccaacaact gcgtaacatt | 120 |
| agcccgccgt gccgctgccc gagcctgcgc aagcggtgc agctgaccca ccagcaacag | 180 |
| ggtcaagtgg gtccgcagca agttcgtcaa atgtatcgtg tggcgagcaa tatcccgagc | 240 |
| acctctagac atcaccatca tcaccactaa | 270 |

<210> SEQ ID NO 25
<211> LENGTH: 35
<212> TYPE: DNA
<213> ORGANISM: Artificial Sequence
<220> FEATURE:
<223> OTHER INFORMATION: MO gene cloning primer forward

<400> SEQUENCE: 25
cggccggtgc acatatgcaa ggtccgggtc gccaa     35

<210> SEQ ID NO 26
<211> LENGTH: 36
<212> TYPE: DNA
<213> ORGANISM: Artificial Sequence
<220> FEATURE:
<223> OTHER INFORMATION: MO gene cloning primer reverse

<400> SEQUENCE: 26

<210> SEQ ID NO 27
<211> LENGTH: 20
<212> TYPE: DNA
<213> ORGANISM: Artificial Sequence
<220> FEATURE:
<223> OTHER INFORMATION: MO gene sequencing primer - forward

<400> SEQUENCE: 27
acggaaatag cgagagatga                                         20

<210> SEQ ID NO 28
<211> LENGTH: 18
<212> TYPE: DNA
<213> ORGANISM: Artificial Sequence
<220> FEATURE:
<223> OTHER INFORMATION: MO gene sequencing primer - reverse

<400> SEQUENCE: 28
ggcagagggc aggttttt                                           18

<210> SEQ ID NO 29
<211> LENGTH: 2710
<212> TYPE: DNA
<213> ORGANISM: Artificial Sequence
<220> FEATURE:
<223> OTHER INFORMATION: pUC57 cloning vector

<400> SEQUENCE: 29
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aaggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt cgagctcggt acctcgcgaa    420
tgcatctaga tatcggatcc cgggcccgtc gactgcagag gcctgcatgc aagcttggcg    480
taatcatggt catagctgtt tcctgtgtga aattgttatc cgctcacaat tccacacaac    540
atacgagccg aagcataaa gtgtaaagcc tggggtgcct aatgagtgag ctaactcaca    600
ttaattgcgt tgcgctcact gcccgctttc cagtcgggaa acctgtcgtg ccagctgcat    660
taatgaatcg gccaacgcgc ggggagaggc ggtttgcgta ttgggcgctc ttccgcttcc    720
tcgctcactg actcgctgcg ctcggtcgtt cggctgcggc gagcggtatc agctcactca    780
aaggcggtaa tacggttatc cacagaatca ggggataacg caggaaagaa catgtgagca    840
aaaggccagc aaaaggccag gaaccgtaaa aaggccgcgt tgctggcgtt tttccatagg    900
ctccgccccc ctgacgagca tcacaaaaat cgacgctcaa gtcagaggtg gcgaaacccg    960
acaggactat aaagatacca ggcgtttccc cctggaagct ccctcgtgcg ctctcctgtt    1020
ccgaccctgc cgcttaccgg atacctgtcc gcctttctcc cttcgggaag cgtggcgctt    1080
tctcatagct cacgctgtag gtatctcagt tcggtgtagg tcgttcgctc caagctgggc    1140
tgtgtgcacg aacccccgt tcagcccgac cgctgcgcct tatccggtaa ctatcgtctt    1200
gagtccaacc cggtaagaca cgacttatcg ccactggcag cagccactgg taacaggatt    1260

```
agcagagcga ggtatgtagg cggtgctaca gagttcttga agtggtggcc taactacggc    1320
tacactagaa gaacagtatt tggtatctgc gctctgctga agccagttac cttcggaaaa    1380
agagttggta gctcttgatc cggcaaacaa accaccgctg gtagcggtgg ttttttttgtt    1440 tgcaagcagc agattacgcg cagaaaaaaa ggatctcaag aagatccttt gatcttttct    1500
acggggtctg acgctcagtg gaacgaaaac tcacgttaag ggattttggt catgagatta    1560
tcaaaaagga tcttcaccta gatccttttg aattaaaaat gaagttttaa atcaatctaa    1620
agtatatatg agtaaacttg gtctgacagt taccaatgct taatcagtga ggcacctatc    1680
tcagcgatct gtctatttcg ttcatccata gttgcctgac tccccgtcgt gtagataact    1740
acgatacggg agggcttacc atctggcccc agtgctgcaa tgataccgcg agacccacgc    1800
tcaccggctc cagatttatc agcaataaac cagccagccg gaagggccga gcgcagaagt    1860
ggtcctgcaa ctttatccgc ctccatccag tctattaatt gttgccggga agctagagta    1920
agtagttcgc cagttaatag tttgcgcaac gttgttgcca ttgctacagg catcgtggtg    1980
tcacgctcgt cgtttggtat ggcttcattc agctccggtt cccaacgatc aaggcgagtt    2040
acatgatccc ccatgttgtg caaaaaagcg gttagctcct tcggtcctcc gatcgttgtc    2100
agaagtaagt tggccgcagt gttatcactc atggttatgg cagcactgca taattctctt    2160
actgtcatgc catccgtaag atgcttttct gtgactggtg agtactcaac caagtcattc    2220
tgagaatagt gtatgcggcg accgagttgc tcttgcccgg cgtcaatacg ggataatacc    2280
gcgccacata gcagaacttt aaaagtgctc atcattggaa aacgttcttc ggggcgaaaa    2340
ctctcaagga tcttaccgct gttgagatcc agttcgatgt aacccactcg tgcacccaac    2400
tgatcttcag catcttttac tttcaccagc gtttctgggt gagcaaaaac aggaaggcaa    2460
aatgccgcaa aaaagggaat aagggcgaca cggaaatgtt gaatactcat actcttcctt    2520
tttcaatatt attgaagcat ttatcagggt tattgtctca tgagcggata catatttgaa    2580
tgtatttaga aaaataaaca aataggggtt ccgcgcacat ttccccgaaa agtgccacct    2640
gacgtctaag aaaccattat tatcatgaca ttaacctata aaaataggcg tatcacgagg    2700
ccctttcgtc                                                          2710
```

<210> SEQ ID NO 30
<211> LENGTH: 5708
<212> TYPE: DNA
<213> ORGANISM: Artificial Sequence
<220> FEATURE:
<223> OTHER INFORMATION: pET-15b expression vector

<400> SEQUENCE: 30

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc cggatatagt tcctcctttc agcaaaaaac ccctcaagac ccgtttagag     240
gccccaaggg gttatgctag ttattgctca gcggtggcag cagccaactc agcttccttt     300
cgggctttgt tagcagccgg atcctcgagc atatggctgc cgcgcggcac caggccgctg     360
ctgtgatgat gatgatgatg gctgctgccc atggtatatc tccttcttaa agttaaacaa     420
aattatttct agaggggaat tgttatccgc tcacaattcc cctatagtga gtcgtattaa     480
tttcgcggga tcgagatctc gatcctctac gccggacgca tcgtggccgg catcaccggc     540
gccacaggtg cggttgctgg cgcctatatc gccgacatca ccgatgggga agatcgggct     600
```

```
cgccacttcg ggctcatgag cgcttgtttc ggcgtgggta tggtggcagg ccccgtggcc    660
gggggactgt tgggcgccat ctccttgcat gcaccattcc ttgcggcggc ggtgctcaac    720
ggcctcaacc tactactggg ctgcttccta atgcaggagt cgcataaggg agagcgtcga    780
gatcccggac accatcgaat ggcgcaaaac ctttcgcggt atggcatgat agcgcccgga    840
agagagtcaa ttcagggtgg tgaatgtgaa accagtaacg ttatacgatg tcgcagagta    900
tgccggtgtc tcttatcaga ccgtttcccg cgtggtgaac caggccagcc acgtttctgc    960
gaaaacgcgg gaaaaagtgg aagcggcgat ggcggagctg aattacattc ccaaccgcgt   1020
ggcacaacaa ctggcgggca aacagtcgtt gctgattggc gttgccacct ccagtctggc   1080
cctgcacgcg ccgtcgcaaa ttgtcgcggc gattaaatct cgcgccgatc aactgggtgc   1140
cagcgtggtg gtgtcgatgg tagaacgaag cggcgtcgaa gcctgtaaag cggcggtgca   1200
caatcttctc gcgcaacgcg tcagtgggct gatcattaac tatccgctgg atgaccagga   1260
tgccattgct gtgaagctg cctgcactaa tgttccggcg ttatttcttg atgtctctga   1320
ccagacaccc atcaacagta ttattttctc ccatgaagac ggtacgcgac tgggcgtgga   1380
gcatctggtc gcattgggtc accagcaaat cgcgctgtta gcgggcccat taagttctgt   1440
ctcggcgcgt ctgcgtctgg ctggctggca taaatatctc actcgcaatc aaattcagcc   1500
gatagcggaa cgggaaggcg actggagtgc catgtccggt tttcaacaaa ccatgcaaat   1560
gctgaatgag ggcatcgttc ccactgcgat gctggttgcc aacgatcaga tggcgctggg   1620
cgcaatgcgc gccattaccg agtccgggct gcgcgttggt gcggatatct cggtagtggg   1680
atacgacgat accgaagaca gctcatgtta tcccgccg ttaaccacca tcaaacagga   1740
ttttcgcctg ctgggcaaa ccagcgtgga ccgcttgctg caactctctc agggccaggc   1800
ggtgaagggc aatcagctgt tgcccgtctc actggtgaaa agaaaaacca ccctggcgcc   1860
caatacgcaa accgcctctc cccgcgcgtt ggccgattca ttaatgcagc tggcacgaca   1920
ggtttcccga ctggaaagcg ggcagtgagc gcaacgcaat taatgtaagt tagctcactc   1980
attaggcacc gggatctcga ccgatgcect tgagagcctt caacccagtc agctccttcc   2040
ggtgggcgcg gggcatgact atcgtcgccg cacttatgac tgtcttcttt atcatgcaac   2100
tcgtaggaca ggtgccggca gcgctctggg tcattttcgg cgaggaccgc tttcgctgga   2160
gcgcgacgat gatcggcctg tcgcttgcgg tattcggaat cttgcacgcc ctcgctcaag   2220
ccttcgtcac tggtcccgcc accaaacgtt tcggcgagaa gcaggccatt atcgccggca   2280
tggcggccga cgcgctgggc tacgtcttgc tggcgttcgc gacgcgaggc tggatggcct   2340
tccccattat gattcttctc gcttccggcg gcatcgggat gccgcgttg caggccatgc   2400 tgtccaggca ggtagatgac gaccatcagg gacagcttca aggatcgctc gcggctctta   2460
ccagcctaac ttcgatcact ggaccgctga tcgtcacggc gatttatgcc gcctcggcga   2520
gcacatggaa cggggttggca tggattgtag gcgccgccct ataccttgtc tgcctccccg   2580
cgttgcgtcg cggtgcatgg agccgggcca cctcgacctg aatggaagcc ggcggcacct   2640
cgctaacgga ttcaccactc caagaattgg agccaatcaa ttcttgcgga gaactgtgaa   2700
tgcgcaaacc aacccttggc agaacatatc catcgcgtcc gccatctcca gcagccgcac   2760
gcggcgcatc tcgggcagcg ttgggtcctg gccacgggtg cgcatgatcg tgctcctgtc   2820
gttgaggacc cggctaggct ggcggggttg ccttactggt tagcagaatg aatcaccgat   2880
acgcgagcga acgtgaagcg actgctgctg caaaacgtct gcgacctgag caacaacatg   2940
```

```
aatggtcttc ggtttccgtg tttcgtaaag tctggaaacg cggaagtcag cgccctgcac    3000
cattatgttc cggatctgca tcgcaggatg ctgctggcta ccctgtggaa cacctacatc    3060
tgtattaacg aagcgctggc attgaccctg agtgattttt ctctggtccc gccgcatcca    3120
taccgccagt tgtttaccct cacaacgttc cagtaaccgg gcatgttcat catcagtaac    3180
ccgtatcgtg agcatcctct ctcgtttcat cggtatcatt accccatga acagaaatcc     3240 cccttacacg gaggcatcag tgaccaaaca ggaaaaaacc gcccttaaca tggcccgctt    3300
tatcagaagc cagacattaa cgcttctgga gaaactcaac gagctggacg cggatgaaca    3360
ggcagacatc tgtgaatcgc ttcacgacca cgctgatgag ctttaccgca gctgcctcgc    3420
gcgtttcggt gatgacggtg aaaacctctg acacatgcag ctcccggaga cggtcacagc    3480
ttgtctgtaa gcggatgccg ggagcagaca agcccgtcag ggcgcgtcag cgggtgttgg    3540
cgggtgtcgg ggcgcagcca tgacccagtc acgtagcgat agcggagtgt atactggctt    3600
aactatgcgg catcagagca gattgtactg agagtgcacc atatatgcgg tgtgaaatac    3660
cgcacagatg cgtaaggaga aaataccgca tcaggcgctc ttccgcttcc tcgctcactg    3720
actcgctgcg ctcggtcgtt cggctgcggc gagcggtatc agctcactca aaggcggtaa    3780
tacggttatc cacagaatca ggggataacg caggaaagaa catgtgagca aaaggccagc    3840
aaaaggccag gaaccgtaaa aaggccgcgt tgctggcgtt tttccatagg ctccgccccc    3900
ctgacgagca tcacaaaaat cgacgctcaa gtcagaggtg gcgaaacccg acaggactat    3960
aaagatacca ggcgtttccc cctggaagct ccctcgtgcg ctctcctgtt ccgaccctgc    4020
cgcttaccgg atacctgtcc gcctttctcc cttcgggaag cgtggcgctt tctcatagct    4080
cacgctgtag gtatctcagt tcggtgtagg tcgttcgctc caagctgggc tgtgtgcacg    4140
aaccccccgt tcagcccgac cgctgcgcct tatccggtaa ctatcgtctt gagtccaacc    4200
cggtaagaca cgacttatcg ccactggcag cagccactgg taacaggatt agcagagcga    4260
ggtatgtagg cggtgctaca gagttcttga agtggtggcc taactacggc tacactagaa    4320
ggacagtatt tggtatctgc gctctgctga agccagttac cttcggaaaa agagttggta    4380
gctcttgatc cggcaaacaa accaccgctg gtagcggtgg tttttttgtt tgcaagcagc    4440
agattacgcg cagaaaaaaa ggatctcaag aagatccttt gatcttttct acggggtctg    4500
acgctcagtg gaacgaaaac tcacgttaag ggattttggt catgagatta tcaaaaagga    4560
tcttcaccta gatcctttta aattaaaaat gaagttttaa atcaatctaa agtatatatg    4620
agtaaacttg gtctgacagt taccaatgct taatcagtga ggcacctatc tcagcgatct    4680
gtctatttcg ttcatccata gttgcctgac tccccgtcgt gtagataact acgatacggg    4740
agggcttacc atctggcccc agtgctgcaa tgataccgcg agacccacgc tcaccggctc    4800
cagatttatc agcaataaac cagccagccg gaagggccga gcgcagaagt ggtcctgcaa    4860
ctttatccgc ctccatccag tctattaatt gttgccggga agctagagta agtagttcgc    4920
cagttaatag tttgcgcaac gttgttgcca ttgctgcagg catcgtggtg tcacgctcgt    4980
cgtttggtat ggcttcattc agctccggtt cccaacgatc aaggcgagtt acatgatccc    5040
ccatgttgtg caaaaaagcg gttagctcct tcggtcctcc gatcgttgtc agaagtaagt    5100
tggccgcagt gttatcactc atggttatgg cagcactgca taattctctt actgtcatgc    5160
catccgtaag atgcttttct gtgactggtg agtactcaac caagtcattc tgagaatagt    5220
gtatgcggcg accgagttgc tcttgcccgg cgtcaacacg gataataccg cgccacata    5280 gcagaacttt aaaagtgctc atcattggaa aacgttcttc ggggcgaaaa ctctcaagga    5340
```

```
tcttaccgct gttgagatcc agttcgatgt aacccactcg tgcacccaac tgatcttcag    5400
catcttttac tttcaccagc gtttctgggt gagcaaaaac aggaaggcaa aatgccgcaa    5460
aaaagggaat aagggcgaca cggaaatgtt gaatactcat actcttcctt tttcaatatt    5520
attgaagcat ttatcagggt tattgtctca tgagcggata catatttgaa tgtatttaga    5580
aaaataaaca aatagggggtt ccgcgcacat ttccccgaaa agtgccacct gacgtctaag    5640
aaaccattat tatcatgaca ttaacctata aaaataggcg tatcacgagg ccctttcgtc    5700
ttcaagaa                                                              5708
```

<210> SEQ ID NO 31
<211> LENGTH: 5938
<212> TYPE: DNA
<213> ORGANISM: Artificial Sequence
<220> FEATURE:
<223> OTHER INFORMATION: pBE-S DNA vector
<220> FEATURE:
<221> NAME/KEY: misc_feature
<222> LOCATION: (198)..(284)
<223> OTHER INFORMATION: aprE SP
<220> FEATURE:
<221> NAME/KEY: misc_feature
<222> LOCATION: (284)..(285)
<223> OTHER INFORMATION: SP cleavage site
<220> FEATURE:
<221> NAME/KEY: misc_feature
<222> LOCATION: (297)..(356)
<223> OTHER INFORMATION: MCS
<220> FEATURE:
<221> NAME/KEY: misc_feature
<222> LOCATION: (357)..(374)
<223> OTHER INFORMATION: His-Tag

<400> SEQUENCE: 31

```
actagtgttc ttttctgtat gaaaatagtt atttcgagtc tctacggaaa tagcgagaga      60
tgatataccT aaatagagat aaaatcatct caaaaaaatg ggtctactaa aatattattc     120
catctattac aataaattca cagaatagtc ttttaagtaa gtctactctg aacttaagca     180
aaaggagagg gacgcgtgtg agaagcaaaa aattgtggat cagcttgttg tttgcgttaa     240
cgttaatctt tacgatggcg ttcagcaaca tgtctgcgca ggctgcggcc ggtgcacata     300
tggagctcgg tacccctcgag ggatccgaat tcaagcttgt cgacctgcag tctagacatc    360
accatcatca ccactaatgc ggtagtttat cacagttaaa ttgctaacgc agtcaggcac     420
cgtgtatgaa atctaacaat gcgctcatcg tcatcctcgg caccgtcacc ctggatgctg     480
taggcatagg cttggttatg ccggtactgc cgggcctatt tcacttttttg cattctacaa    540 actgcataac tattatgtaa atcgctcctt tttaggtggc acaaatgtga ggcattttcg     600
ctctttccgg caaccacttc caagtaaagt ataacacact atactttata ttcataaagt     660
gtgtgctctg cgaggctgtc ggcagtgccg accaaaacca taaaaccttt aagacctttc     720
ttttttttac gagaaaaaag aaacaaaaaa acctgccctc tgccacctca gcaaggggg     780 gttttgctct cgtgctcgtt taaaaatcag caagggacag gtagtatttt tgagaagat     840 cactcaaaaa atctccacct ttaaaccctt gccaattttt attttgtccg ttttgtctag     900
cttaccgaaa gccagactca gcaagaataa aattttatt gtctttcggt tttctagtgt    960
aacggacaaa accactcaaa ataaaaaaga tacaagagag gtctctcgta tcttttattc    1020
agcaatcgcg cccgattgct gaacagatta ataatagatt ttagcttttt atttgttgaa    1080
aaaagctaat caaattgttg tcgggatcaa ttactgcaaa gtctcgttca tcccaccact   1140
```

-continued

```
gatcttttaa tgatgtattg gggtgcaaaa tgcccaaagg cttaatatgt tgatataatt    1200
catcaattcc ctctacttca atgcggcaac tagcagtacc agcaataaac gactccgcac    1260
ctgtacaaac cggtgaatca ttactacgag agcgccagcc ttcatcactt gcctcccata    1320
gatgaatccg aacctcatta cacattagaa ctgcgaatcc atcttcatgg tgaaccaaag    1380
tgaaacctag tttatcgcaa taaaaaccta tactcttttt aatatccccg actggcaatg    1440
ccgggataga ctgtaacatt ctcacgcata aaatcccctt tcattttcta atgtaaatct    1500
attaccttat tattaattca attcgctcat aattaatcct ttttcttatt acgcaaaatg    1560
gcccgattta agcacaccct ttattccgtt aatgcgccat gacagccatg ataattacta    1620
atactaggag aagttaataa atacgagcaa aaggccagca aaaggccagg aaccgtaaaa    1680
aggccgcgtt gctggcgttt ttccataggc tccgccccc  tgacgagcat cacaaaaatc    1740
gacgctcaag tcagaggtgg cgaaacccga caggactata agataccag  gcgtttcccc    1800 ctggaagctc cctcgtgcgc tctcctgttc cgaccctgcc gcttaccgga tacctgtccg    1860
cctttctccc ttcgggaagc gtggcgcttt ctcatagctc acgctgtagg tatctcagtt    1920
cggtgtaggt cgttcgctcc aagctgggct gtgtgcacga accccccgtt cagcccgacc    1980
gctgcgcctt atccggtaac tatcgtcttg agtccaaccc ggtaagacac gacttatcgc    2040
cactggcagc agccactggt aacaggatta gcagagcgag gtatgtaggc ggtgctacag    2100
agttcttgaa gtggtggcct aactacggct acactagaag aacagtattt ggtatctgcg    2160
ctctgctgaa gccagttacc ttcggaaaaa gagttggtag ctcttgatcc ggcaaacaaa    2220
ccaccgctgg tagcggtggt ttttttgttt gcaagcagca gattacgcgc agaaaaaaag    2280
gatctcaaga agatcctttg atcttttcta cggggtctga cgctcagtgg aacgaaaact    2340
cacgttaagg gattttggtc atgagattat caaaaaggat cttcacctag atccttttaa    2400
attaaaaatg aagttttaaa tcaatctaaa gtatatatga gtaaacttgg tctgacagtt    2460
accaatgctt aatcagtgag gcacctatct cagcgatctg tctatttcgt tcatccatag    2520
ttgcctgact ccccgtcgtg tagataacta cgatacggga gggcttacca tctggcccca    2580
gtgctgcaat gataccgcga acccacgct  caccggctcc agatttatca gcaataaacc    2640
agccagccgg aagggccgag cgcagaagtg gtcctgcaac tttatccgcc tccatccagt    2700
ctattaattg ttgccgggaa gctagagtaa gtagttcgcc agttaatagt ttgcgcaacg    2760
ttgttgccat tgctacaggc atcgtggtgt cacgctcgtc gtttggtatg gcttcattca    2820
gctccggttc ccaacgatca aggcgagtta catgatcccc catgttgtgc aaaaaagcgg    2880
ttagctcctt cggtcctccg atcgttgtca gaagtaagtt ggccgcagtg ttatcactca    2940
tggttatggc agcactgcat aattctctta ctgtcatgcc atccgtaaga tgcttttctg    3000
tgactggtga gtactcaacc aagtcattct gagaatagtg tatgcggcga ccgagttgct    3060
cttgcccggc gtcaatacgg gataataccg cgccacatag cagaacttta aaagtgctca    3120
tcattggaaa acgttcttcg gggcgaaaac tctcaaggat cttaccgctg ttgagatcca    3180
gttcgatgta acccactcgt gcacccaact gatcttcagc atcttttact ttcaccagcg    3240
tttctgggtg agcaaaaaca ggaaggcaaa atgccgcaaa aaagggaata agggcgacac    3300
ggaaatgttg aatactcata ctcttccttt ttcaatatta ttgaagcatt tatcagggtt    3360
attgtctcat gagcggatac atatttgaat gtatttagaa aaataaacaa ataggggttc    3420
cgcgcacatt tccccgaaaa gtgccacctg acgtctaaga aaccattatt atcatgacat    3480
taacctataa aaataggcgt atcacgaggc cctttcgtct cgcgcgtttc ggtgatgacg    3540
```

-continued

```
gtgaaaacct ctgacagtaa ccaacatgat taacaattat tagaggtcat cgttcaaaat    3600
ggtatgcgtt ttgacacatc cactatatat ccgtgtcgtt ctgtccactc ctgaatccca    3660
ttccagaaat tctctagcga ttccagaagt ttctcagagt cggaaagttg accagacatt    3720
acgaactggc acagatggtc ataacctgaa ggaagatctg attgcttaac tgcttcagtt    3780
aagaccgaag cgctcgtcgt ataacagatg cgatgatgca gaccaatcaa catggcacct    3840
gccattgcta cctgtacagt caaggatggt agaaatgttg tcggtccttg cacacgaata    3900
ttacgccatt tgcctgcata ttcaaacagc tcttctacga taagggcaca aatcgcatcg    3960
tggaacgttt gggcttctac cgatttagca gtttgataca ctttctctaa gtatccacct    4020
gaatcataaa tcggcaaaat agagaaaaat tgaccatgtg taagcggcca atctgattcc    4080
acctgagatg cataatctag tagaatctct tcgctatcaa aattcacttc caccttccac    4140
tcaccggttg tccattcatg gctgaactct gcttcctctg ttgacatgac acacatcatc    4200
tcaatatccg aatagggccc atcagtctga cgaccaagag agccataaac accaatagcc    4260
ttaacatcat ccccatattt atccaatatt cgttccttaa tttcatgaac aatcttcatt    4320
ctttcttctc tagtcattat tattggtcca ttcactattc tcattccctt ttcagataat    4380
tttagatttg ctttttctaaa taagaatatt tggagagcac cgttcttatt cagctattaa    4440
taactcgtct tcctaagcat ccttcaatcc ttttaataac aattatagca tctaatcttc    4500
aacaaactgg cccgttttgtt gaactactct ttaataaaat aatttttccg ttcccaattc    4560
cacattgcaa taatagaaaa tccatcttca tcggcttttt cgtcatcatc tgtatgaatc    4620
aaatcgcctt cttctgtgtc atcaaggttt aatttttat gtatttcttt taacaaacca    4680
ccataggaga ttaaccttttt acggtgtaaa ccttcctcca aatcagacaa acgtttcaaa    4740 ttctttttctt catcatcggt cataaaatcc gtatcctta caggatattt tgcagtttcg    4800
tcaattgccg attgtatatc cgatttatat ttattttcg gtcgaatcat ttgaactttt    4860
acatttggat catagtctaa tttcattgcc ttttccaaa attgaatcca ttgttttga     4920 ttcacgtagt tttctgtatt cttaaaataa gttggttcca cacataccaa tacatgcatg    4980
tgctgattat aagaattatc tttattattt attgtcactt ccgttgcacg cataaaacca    5040
acaagatttt tattaatttt tttatattgc atcattcggc gaaatccttg agccatatct    5100
gacaaactct tatttaattc ttcgccatca taaacatttt taactgttaa tgtgagaaac    5160
aaccaacgaa ctgttggctt ttgtttaata acttcagcaa caaccttttg tgactgaatg    5220
ccatgtttca ttgctctcct ccagttgcac attggacaaa gcctggattt acaaaaccac    5280
actcgataca actttctttc gcctgtttca cgattttgtt tatactctaa tatttcagca    5340
caatctttta ctctttcagc ctttttaaat tcaagaatat gcagaagttc aaagtaatca    5400
acattagcga ttttctttttc tctccatggt ctcacttttc cacttttgt cttgtccact    5460 aaaaccttg attttcatc tgaataaatg ctactattag gacacataat attaaaagaa    5520 accccatct atttagttat ttgtttagtc acttataact ttaacagatg gggttttctt    5580
gtgcaaccaa ttttaagggt tttcaatact ttaaaacaca tacataccaa cacttcaacg    5640
cacctttcag caactaaaat aaaaatgacg ttatttctat atgtatcaag ataagaaaga    5700
acaagttcaa aaccatcaaa aaaagacacc ttttcaggtg cttttttttat tttataaact    5760
```

```
cattccctga tctcgacttc gttctttttt tacctctcgg ttatgagtta gttcaaattc    5820
gttcttttta ggttctaaat cgtgtttttc ttggaattgt gctgttttat cctttacctt    5880
gtctacaaac cccttaaaaa cgtttttaaa ggcttttaag ccgtctgtac gttcctaa      5938
```